US010602978B2

(12) United States Patent
Purdon et al.

(10) Patent No.: US 10,602,978 B2
(45) Date of Patent: Mar. 31, 2020

(54) SYSTEMS AND METHODS FOR IMPROVED BRAIN MONITORING DURING GENERAL ANESTHESIA AND SEDATION

(71) Applicants: Patrick L. Purdon, Somerville, MA (US); Emery N. Brown, Brookline, MA (US); Oluwaseun Johnson-Akeju, Dorchester, MA (US)

(72) Inventors: Patrick L. Purdon, Somerville, MA (US); Emery N. Brown, Brookline, MA (US); Oluwaseun Johnson-Akeju, Dorchester, MA (US)

(73) Assignee: The General Hospital Corporation, Boston, MA (US)

( * ) Notice: Subject to any disclaimer, the term of this patent is extended or adjusted under 35 U.S.C. 154(b) by 900 days.

(21) Appl. No.: 14/485,523

(22) Filed: Sep. 12, 2014

(65) Prior Publication Data

US 2015/0080754 A1 Mar. 19, 2015

Related U.S. Application Data

(60) Provisional application No. 61/877,800, filed on Sep. 13, 2013.

(51) Int. Cl.
*A61B 5/0476* (2006.01)
*A61B 5/00* (2006.01)
(Continued)

(52) U.S. Cl.
CPC ............ *A61B 5/4821* (2013.01); *A61B 5/048* (2013.01); *A61B 5/04012* (2013.01);
(Continued)

(58) Field of Classification Search
CPC .... A61B 5/0476; A61B 5/4821; A61B 5/4806
See application file for complete search history.

(56) References Cited

U.S. PATENT DOCUMENTS

| 2,507,631 A | 5/1950 | Hartmann et al. |
| 2,957,880 A | 10/1960 | Rometsch |

(Continued)

FOREIGN PATENT DOCUMENTS

| EP | 0765630 A1 | 4/1997 |
| JP | 2008178546 A | 8/2008 |

(Continued)

OTHER PUBLICATIONS

Absalom, et al., Closed-Loop Control of Anesthesia Using Bispectral Index, Anesthesiology, 2002, 96(1):67-73.
(Continued)

*Primary Examiner* — Puya Agahi
(74) *Attorney, Agent, or Firm* — Quarles & Brady LLP

(57) ABSTRACT

Systems and method for age-compensated monitoring of a patient experiencing administration of at least one drug having anesthetic properties are provided. In one embodiment, a system includes a plurality of sensors configured to acquire physiological data from the patient and at least one processor configured to receive the physiological data from the plurality of sensors, and determine, from the physiological data, signal markers indicative of an apparent or likely patient age. The at least one processor is also configured to at least one of scale and regulate the physiological data using at least the apparent patient age to create age-compensated data, and generate a report including the age-compensated data.

17 Claims, 20 Drawing Sheets
(16 of 20 Drawing Sheet(s) Filed in Color)

(51) Int. Cl.
*A61B 5/04* (2006.01)
*A61B 5/048* (2006.01)
*G16H 15/00* (2018.01)

(52) U.S. Cl.
CPC .......... *A61B 5/0476* (2013.01); *A61B 5/4806* (2013.01); *A61B 5/7257* (2013.01); *G16H 15/00* (2018.01)

(56) References Cited

U.S. PATENT DOCUMENTS

| | | | |
|---|---|---|---|
| 4,195,643 | A | 4/1980 | Pratt, Jr. |
| 4,392,849 | A | 7/1983 | Petre et al. |
| 4,448,199 | A | 5/1984 | Schmid |
| 4,911,167 | A | 3/1990 | Corenman et al. |
| 5,195,530 | A | 3/1993 | Shindel |
| 5,851,438 | A | 12/1998 | Chan |
| 5,908,850 | A | 6/1999 | Zeitlin et al. |
| 6,025,362 | A | 2/2000 | Fukunaga et al. |
| 6,032,063 | A | 2/2000 | Hoar et al. |
| 6,032,065 | A | 2/2000 | Brown |
| 6,067,467 | A | 5/2000 | John |
| 6,281,242 | B1 | 8/2001 | Regan et al. |
| 6,338,713 | B1 | 1/2002 | Chamoun et al. |
| 6,708,051 | B1 | 3/2004 | Durousseau |
| 6,740,214 | B1 | 5/2004 | Dobson et al. |
| 6,944,565 | B2 | 9/2005 | Meneilage et al. |
| 7,006,872 | B2 | 2/2006 | Gielen et al. |
| 7,286,871 | B2 | 10/2007 | Cohen |
| 7,783,343 | B2 | 8/2010 | Sarkela et al. |
| 8,025,404 | B2 | 9/2011 | Bolger et al. |
| 8,073,534 | B2 | 12/2011 | Low |
| 8,244,526 | B2 | 8/2012 | Vos et al. |
| 8,298,154 | B2 | 10/2012 | Hete et al. |
| 8,315,970 | B2 | 11/2012 | Zalay et al. |
| 8,521,294 | B2 | 8/2013 | Sarma et al. |
| 8,630,722 | B2 | 1/2014 | Condurso et al. |
| 2002/0128798 | A1 | 9/2002 | Lange et al. |
| 2002/0156357 | A1 | 10/2002 | Axelgaard |
| 2003/0088167 | A1 | 5/2003 | Fendrock et al. |
| 2003/0130585 | A1 | 7/2003 | Wenger |
| 2004/0143021 | A1 | 7/2004 | Larijani |
| 2004/0193068 | A1 | 9/2004 | Burton et al. |
| 2005/0054941 | A1 | 3/2005 | Ting et al. |
| 2006/0135880 | A1 | 6/2006 | Sarkela |
| 2006/0178585 | A1 | 8/2006 | Sharrock |
| 2006/0229519 | A1 | 10/2006 | Fujiwara et al. |
| 2007/0067003 | A1 | 3/2007 | Sanchez et al. |
| 2007/0073355 | A1 | 3/2007 | Dilorenzo |
| 2007/0100389 | A1 | 5/2007 | Jaax et al. |
| 2007/0123468 | A1 | 5/2007 | Jenkins |
| 2007/0150025 | A1 | 6/2007 | Dilorenzo et al. |
| 2007/0167694 | A1 | 7/2007 | Causevic et al. |
| 2007/0191704 | A1 | 8/2007 | DeCharms |
| 2007/0203540 | A1 | 8/2007 | Goetz et al. |
| 2008/0021345 | A1 | 1/2008 | Kern et al. |
| 2008/0249431 | A1 | 10/2008 | Bier et al. |
| 2008/0306397 | A1 | 12/2008 | Bonmassar et al. |
| 2010/0023089 | A1 | 1/2010 | DiLorenzo |
| 2010/0280333 | A1 | 11/2010 | Parshuram et al. |
| 2011/0044524 | A1 | 2/2011 | Wang et al. |
| 2011/0082381 | A1 | 4/2011 | Uthman et al. |
| 2011/0118620 | A1* | 5/2011 | Scheib ................... A61B 5/048 600/544 |
| 2011/0125046 | A1 | 5/2011 | Burton et al. |
| 2011/0137134 | A1 | 6/2011 | Hemmerling et al. |
| 2011/0137297 | A1 | 6/2011 | Kiani et al. |
| 2011/0218454 | A1 | 9/2011 | Low |
| 2011/0224570 | A1 | 9/2011 | Causevic |
| 2012/0022391 | A1 | 1/2012 | Leuthardt |
| 2012/0029378 | A1 | 2/2012 | Low |
| 2012/0101401 | A1 | 4/2012 | Faul et al. |
| 2012/0250963 | A1 | 10/2012 | Carroll et al. |
| 2013/0131464 | A1 | 5/2013 | Westbrook et al. |
| 2013/0197339 | A1 | 8/2013 | Bardakjian et al. |
| 2013/0211224 | A1 | 8/2013 | Isenhart et al. |
| 2013/0310422 | A1 | 11/2013 | Brown et al. |
| 2013/0331660 | A1* | 12/2013 | Al-Ali ................... A61B 5/0476 600/301 |
| 2014/0012100 | A1 | 1/2014 | Al-Ali et al. |
| 2014/0180160 | A1 | 6/2014 | Brown et al. |
| 2014/0187973 | A1 | 7/2014 | Brown et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2014/0371548 | A1 | 12/2014 | Al-Ali et al. |
| 2014/0379620 | A1* | 12/2014 | Sarrafzadeh ......... A61B 5/7264 706/12 |
| 2015/0011907 | A1 | 1/2015 | Purdon et al. |
| 2015/0080754 | A1 | 3/2015 | Purdon et al. |

FOREIGN PATENT DOCUMENTS

| | | | |
|---|---|---|---|
| RU | 95243 | U1 | 6/2010 |
| WO | 2004036379 | A2 | 4/2004 |
| WO | 2004037114 | A2 | 5/2004 |
| WO | 2004047632 | A1 | 6/2004 |
| WO | 2012145285 | A1 | 10/2012 |
| WO | 2012154701 | A1 | 11/2012 |
| WO | WO-2012154701 | A1 * | 11/2012 ........... A61B 5/0476 |

OTHER PUBLICATIONS

Absalom, et al., Closed Loop Anesthesia: Are We Getting Close to Finding the Holy Grail?, Anesthesia & Analgesia, 2011, 112(3):516-518.
Andrews, et al., The Chronux Manual, Aug. 16, 2008, 178 pages.
Araki, et al., Computer Control of Physiological States of Patients Under and After Surgical Operation, Annual Reviews in Control, 2005, 29:229-236.
Barras, et al., Total Intravenous Anesthesia on the Battlefield, The Army Medical Department Journal, 2009, pp. 68-72.
Bellville, et al., Servo Control of General Anesthesia, Science, 1957, 126:827-830.
Besch, et al., Occurrence of and Risk Factors for Electroencephalogram Burst Suppression During Propofol-Remifentanil Anaesthesia, British Journal of Anaesthesia, Advance Access Published Aug. 8, 2011, 8 pages.
Besthorn, et al., EEG Coherence in Alzheimer Disease, Electroencephalography and Clinical Neurophysiology, 1994, 90:242-245.
Bickford, Automatic Electroencephalographic Control of General Anesthesia, EEG Clin. Neurophysiol., 1950, 2:93-96.
Bickford, Use of Frequency Discrimination in the Automatic Electroencephalographic Control of Anesthesia (Servo-Anesthesia), EEG Clin. Neurophysiol., 1951, 3:83-86.
Blanco, et al., Time-Frequency Analysis of Electroencephalogram Series. III. Wavelet Packets and Information Cost Function, Physical Review E, 1998, 57(1):932-940.
Bonmassar, Resistive Tapered Stripline (RTS) in Electroencephalogram Recordings During MRI, IEEE Transactions on Microwave Theory and Techniques, 2004, 52(8):1992-1998.
Bourguignon, et al., A Sparsity-Based Method for the Estimation of Spectral Lines From Irregularly Sampled Data, IEEE Journal of Selected Topics in Signal Processing, 2007, 1(4):575-585.
Breshears, et al., Stable and Dynamic Cortical Electrophysiology of Induction and Emergence with Propofol Anesthesia, PNAS, 2010, 107(49):21170-21175.
Candes, et al., Enhancing Sparsity by Reweighted l1 Minimization, J. Fourier Anal. Appl., 2008, 14:877-905.
Chemali, et al., Burst Suppression Probability Algorithms: State-Space Methods for Tracking EEG Burst Suppression, J. Neural. Eng., 2013, 10(5):056017.
Ching, et al., A Neurophysiological-Metabolic Model for Burst Suppression, PNAS, 2012, 109(8):3095-3100.
Cimenser, et al., Tracking Brain States Under General Anesthesia by Using Global Coherence Analysis, PNAS, 2011, 108(21):8832-8837.

(56) References Cited

OTHER PUBLICATIONS

Ciuciu, et al., A Half-Quadratic Block-Coordinate Descent Method for Spectral Estimation, Signal Processing, 2002, 82:941-959.
Cotten, et al., Closed-Loop Continuous Infusions of Etomidate and Etomidate Analogs in Rats, Anesthesiology, 2011, 115(4):764-773.
Dodson, et al., Postoperative Effects of Methylphenidate, British Journal of Anaesthesia, 1980, 52:1265-1270.
Gentilini, et al., Modeling and Closed-Loop Control of Hypnosis by Means of Bispectral Index (BIS) with Isoflurane, IEEE Transactions on Biomedical Engineering, 2001, 48(8):874-889.
Glass, Automated Control of Anesthesia Ten Years Later: Futuristic Novelty or Present Day Reality, Can. J. Anesth./J. Can. Anesth., 2010, 57:715-719.
Goldman, et al., Acquiring Simultaneous EEG and Functional MRI, Clinical Neurophysiology, 2000, 111:1974-1980.
Hahn, et al., Closed-Loop Anesthetic Drug Concentration Estimation Using Clinical-Effect Feedback IEEE, Transactions on Biomedical Engineering, 2011, 58(1):3-6.
Hahn, et al., A Direct Dynamic Dose-Response Model of Propofol for Individualized Anesthesia Care, Journal of Latex Class Files, 2007, 6(1):1-8.
Hemmerling, et al., A Randomized Controlled Trial Demonstrates that a Novel Closed-Loop Propofol System Performs Better Hypnosis Control than Manual Administration, Can. J. Anesth./J. Can. Anesth., 2010, 57:725-735.
John, et al., Invariant Reversible QEEG Effects of Anesthetics, Consciousness and Cognition, 2001, 10:165-183.
LeMieux, et al., Recording of EEG During fMRI Experiments: Patient Safety, MRM, 1997, 38:943-952.
Leslie, et al., Closed Loop Control of Sedation for Colonoscopy Using the Bispectral Index, Anaesthesia, 2002, 57:690-709.
Liley, et al., Propofol and Remifentanil Differentially Modulate Frontal Electroencephalographic Activity, Anesthesiology, 2010, 113:292-304.
Lin, et al., EEG-Based Drowsiness Estimation for Safety Driving Using Independent Component Analysis, IEEE Transactions on Circuits and Systems—I: Regular Papers, 2005, 52(12):2726-2738.
Liu, et al., Titration of Propofol for Anesthetic Induction and Maintenance Guided by the Bispectral Index: Closed-Loop Versus Manual Control, Anesthesiology, 2006, 104:686-695.
Liu, et al., Feasibility of Closed-Loop Titration of Propofol Guided by the Bispectral Index for General Anaesthesia Induction: A Prospective Randomized Study, European Journal of Anaesthesiology, 2006, 23:465-469.
Liu, et al., Neural Origin of Spontaneous Hemodynamic Fluctuations in Rats Under Burst-Suppression Anesthesia Condition, Cerebral Cortex, 2011, 21:374-384.
Locher, et al., A New Closed-Loop Control System for Isoflurane Using Bispectral Index Outperforms Manual Control, Anesthesiology, 2004, 101:591-602.
Lotte, et al., A Review of Classification Algorithms for EEG-Based Brain-Computer Interfaces, Journal of Neural Engineering, 2007, 4:R1-R13.
Martin, et al., Investigating Neural-Hemodynamic Coupling and the Hemodynamic Response Function in the Awake Rat, NeuroImage, 2006, 32:33-48.
Mirsattari, et al., Treatment of Refractory Status Epilepticus With Inhalational Anesthetic Agents Isoflurane and Desflurane, Arch. Neurol., 2004, 61:1254-1259.
Molaee-Ardekani, et al., Delta Waves Differently Modulate High Frequency Components of EEG Oscillations in Various Unconsciousness Levels, Proceedings of the 29th Annual International Conference of the IEEE EMBS, 2007, pp. 1294-1297.
Morley, et al., Closed Loop Control of Anaesthesia: An Assessment of the Bispectral Index as the Target of Control, Anaesthesia, 2000, 55:953-959.
Mortier, et al., Closed-Loop Controlled Administration of Propofol Using Bispectral Analysis, Anesthesia, 1998, 53:749-754.
Orsini, et al., Propofol Infusion Syndrome: Case Report and Literature Review, Am. J. Health-Syst. Pharm., 2009, 66:908-915.
Pritchett, et al., Power Analysis of Gamma Frequencies (30-47Hz), Adjusting for Muscle Activity (80-97Hz), in Anesthesia: A Comparison Between Young Adults, Middle-Aged and the Elderly, 30th Annual International IEEE EMBS Conference, 2008, pp. 825-830.
Purdon, Multimodal Neuroimaging with Simultaneous Electroencephalogram and High-Field Functional Magnetic Resonance Imaging, Master Thesis Submitted to the Harvard-MIT Division of Health Sciences and Technology, Jun. 2005.
Purdon, et al., Electroencephalogram Signatures of Loss and Recovery of Consciousness from Propofol, PNAS, Published Online Mar. 4, 2013, pp. E1142-E1151.
Puri, et al., Closed-Loop Anaesthesia Delivery System (CLADS(TM)) Using Bispectral Index: A Performance Assessment Study, Anaesthesia and Intensive Care, 2007, 35(3):357-362.
Roche-Labarbe, et al., Coupled Oxygenation Oscillation Measured by NIRS and Intermittent Cerebral Activation on EEG in Premature Infants, NeuroImage, 2007, 36:718-727.
Rossetti, et al., Refractory Status Epilepticus, Effect of Treatment Aggressiveness on Prognosis, Arch. Neurol., 2005, 62:1698-1702.
Sacchi, et al., Interpolation and Extrapolation Using a High-Resolution Discrete Fourier Transform, IEEE Transactions on Signal Processing, 1998, 46(1)31-38.
Sartori, et al., On-Line Estimation of Propofol Pharmacodynamic Parameters, Proceedings of the 2005 IEEE Engineering in Medicine and Biology 27th Annual Conference, 2005, pp. 74-77.
Sawaguchi, et al., A Model-Predictive Hypnosis Control System Under Total Intravenous Anesthesia, IEEE Transactions on Biomedical Engineering, 2008, 55(3):874-887.
Schaffer, et al., The Effect of the Atmosphere and the Role of Pore Filling on the Sintering of Aluminum, Acta Materialia, 2006, 54(1):131-138.
Schwilden, et al., Closed-Loop Feedback Control of Methohexital Anesthesia by Quantitative EEG Analysis in Humans, Anesthesiology, 1987, 67:341-347.
Schwilden, et al., Closed-Loop Feedback Control of Propofol Anaesthesia by Quantitative EEG Analysis in Humans, Br. J. Anaesth., 1989, 62:290-296.
Struys, et al., Comparison of Closed-Loop Controlled Administration of Propofol Using Bispectral Index as the Controlled Variable Versus "Standard Practice" Controlled Administration, Anesthesiology, 2001, 95(1):6-17.
Struys, et al., Closed Loops in Anaesthesia, Best Practice & Research Clinical Anaesthesiology, 2006, 20(1):211-220.
Tan, et al., Sparse Learning Via Iterative Minimization With Application to MIMO Radar Imaging, IEEE Transactions on Signal Processing, 2011, 59(3)1088-1101.
Truccolo, et al., A Point Process Framework for Relating Neural Spiking Activity to Spiking History, Neural Ensemble, and Extrinsic Covariate Effects, J. Neurophysiol., 2005, 93:1074-1089.
Van Vugt, Comparison of Spectral Analysis Methods for Characterizing Brain Oscillations, J. Neurosci. Methods, 2007, 162(1-2):49-63.
Vijn, et al., I.v. Anaesthesia and EEG Burst Suppression in Rats: Bolus Injections and Closed-Loop Infusions, British Journal of Anaesthesia, 1998, 81:415-421.
Vusanovic, et al., Microsegregation Phenomena in Al—Cu—Mg Alloy with Considering of Diffusion Phenomena in Primary Phase, Facta Universitatis, Series: Mechanical Engineering, 2001, 1(8):965-980.
Wang, et al., Precipitates and Intermetallic Phases in Precipitation and Hardening Al—Cu—Mg—(Li) Based Alloys, International Materials Reviews, 2005, 50(4):193-215.
Zdunek, et al., Improved M-FOCUSS Algorithm With Overlapping Blocks for Locally Smooth Sparse Signals, IEEE Transactions on Signal Processing, 2008, 56(10):4752-4761.
Article: "Polyesters", http://web.archive.org/web/20020812093256/http://pslc.ws/macrog/pet.htm, Copyright 1995, 1996 Department of Polymer Science, University of Southern Mississippi, 4 pages.
European Patent Office, Extended European Search Report, Application No. 12781958.9, dated Sep. 15, 2014, 12 pages.
PCT International Search Report and Written Opinion, PCT/US2005/042401, dated Jun. 14, 2006, 17 pages.

(56) References Cited

OTHER PUBLICATIONS

PCT International Search Report and Written Opinion, PCT/US2009/062072, dated May 12, 2010, 13 pages.
PCT International Search Report and Written Opinion, PCT/US2011/050213, dated May 1, 2012, 12 pages.
PCT International Search Report and Written Opinion, PCT/US2012/036854, dated Aug. 16, 2012, 6 pages.
PCT International Search Report and Written Opinion, PCT/US2013/064852, dated Jan. 23, 2014, 6 pages.
PCT International Search Report and Written Opinion, PCT/US2014/033619, dated Sep. 23, 2014, 12 pages.
PCT International Search Report and Written Opinion, PCT/US2014/035166, dated Aug. 29, 2014, 17 pages.
PCT International Search Report and Written Opinion, PCT/US2014/035178, dated Sep. 15, 2014, 15 pages.
PCT International Search Report and Written Opinion, PCT/US2014/035319, dated Sep. 26, 2014, 15 pages.
PCT International Search Report and Written Opinion, PCT/US2014/035329, dated Sep. 26, 2014, 11 pages.
PCT International Search Report and Written Opinion, PCT/US2014/035333, dated Sep. 26, 2014, 14 pages.
PCT International Search Report and Written Opinion, PCT/US2014/044692, dated Nov. 4, 2014, 12 pages.
PCT International Search Report and Written Opinion, PCT/US2014/044720, dated Nov. 28, 2014, 13 pages.
PCT International Search Report and Written Opinion, PCT/US2014/055509, dated Dec. 2, 2014, 15 pages.
PCT International Search Report and Written Opinion, PCT/US2014/064144, dated Jan. 27, 2015, 7 pages.

* cited by examiner

SYSTEMS AND METHODS FOR IMPROVED BRAIN MONITORING DURING GENERAL ANESTHESIA AND SEDATION

CROSS-REFERENCE TO RELATED APPLICATIONS

This application is based on, claims priority to, and incorporates herein by reference in its entirety U.S. Provisional Application Ser. No. 61/877,800, filed Sep. 13, 2013, and entitled, "SYSTEM AND METHOD FOR AGE-APPROPRIATE BRAIN MONITORING DURING GENERAL ANESTHESIA AND SEDATION."

STATEMENT REGARDING FEDERALLY SPONSORED RESEARCH

This invention was made with Government support under Grant Numbers OD000654, RR014075, GM104948, GM007592, EB001954, EB002482, EB006385, OD003646, OD006454, awarded by the National Institutes of Health. The Government has certain rights in the invention.

BACKGROUND OF THE INVENTION

The present disclosure is generally directed to systems and methods for monitoring patients states and, more particularly, relates to systems and methods for monitoring and controlling patients states during medical interventions, evaluations or procedures, such as receiving anesthesia or sedation, and using patient-specific information.

SUMMARY OF THE INVENTION

The present disclosure provides systems and methods for monitoring and controlling patients using acquired physiological data, for use associated certain medical interventions, evaluations or procedures, such as general anesthesia and sedation. Specifically, the present invention provides systems and methods capable of accurate brain monitoring, achieved via patient-specific characteristics identified in the physiological data.

A brain monitoring approach, in accordance with aspects of the present disclosure, may be capable of determining patient characteristics, based on measured brain signals, activity or functionality, and adjust a data acquisition process, modify a display, or perform an analysis based on the determined patient characteristics. For example, determined patient characteristics can include an apparent or likely patient age, which can be similar or different from the patient's real age, as well as other patient information.

By way of example, systems and methods described herein may be used to appropriately scale, modify and visualize acquired data. Also, systems and methods described may be used to generate compensated data, such as age-appropriate data, and conduct an accurate analysis based on the compensated or appropriately modified or adapted data. By way of example, a patient condition or predisposition may be assessed using an approach described herein. Specifically, patients potentially at higher risk for post-operative cognitive conditions or disorders may be pre-operatively identified, and given certain indications, such as specific regimens for anesthetic, post-anesthetic, or intensive care, using information provided using systems and methods herein. In addition, such an approach may be used to monitor anesthetic responses in children to achieve anesthetic or sedative states reflecting the unique level of development in brain circuits associated with different ages, age ranges, and a patient's specific level of development.

In accordance with one aspects of the disclosure, a system for age-compensated monitoring of a patient experiencing an administration of at least one drug having anesthetic properties is provided. The system includes a plurality of sensors configured to acquire physiological data from the patient while receiving the at least one drug having anesthetic properties, and at least one processor configured to acquire physiological data from the plurality of sensors, and determine, from the physiological data, signal markers at least consistent with a patient age. The at least one processor is also configured to generate a report including at least the physiological data adjusted for the patient age based on at least one of the signal markers. In some aspects, the processor is further configured to identify signatures related to at least one of an amplitude and a power spectrum to determine the signal markers from the physiological data, adjust at least one of an amplifier gain and a scale for the report including at least the physiological data in based on at least one of the signal markers and the indication, assemble the physiological data into time-series data using a multitaper approach to account for a dynamic range of signals spanning several orders of magnitude. The system may further include a user interface configured to receive an indication of at least one characteristic of the patient and wherein the processor is further configured to adjust for the patient age based on the at least one a characteristic of the patient.

In accordance with another aspect of the disclosure, a method for age-compensated monitoring of a patient experiencing an administration of at least one drug having anesthetic properties is provided. The method includes acquiring scout data from the plurality of sensors, determining, from the scout data, a patient age, and acquiring physiological data from the plurality of sensors. The method also includes generating a report including the physiological data at least one of scaled and reported against a scale based on the patient age. In some aspects, determining the patient age includes determining signal markers from the scout data related to at least one of an amplitude and a power spectrum and comparing the signal markers against an age indicator. The method may also include regulating acquisition of the physiological data based on the patient age, wherein regulating includes adjusting at least one amplifier gain based on the patient age, and performing a multitaper analysis to account for a dynamic range of signals spanning several orders of magnitude.

In accordance with another aspect of the disclosure, a system for age-compensated monitoring of a patient experiencing an administration of at least one drug having anesthetic properties is provided. The system includes a plurality of sensors configured to acquire physiological data from the patient, and at least one processor configured to receive the physiological data from the plurality of sensors, and determine, from the physiological data, signal markers indicative of an apparent patient age. The at least one processor is also configured to at least one of scale or regulate the physiological data using at least the apparent patient age to create age-compensated data, and generate a report including the age-compensated data. In some aspects, the processor is further configured to identify signatures related to at least one of an amplitude and a power spectrum to determine the signal makers, adjust at least one amplifier gain in accordance with the signal markers to scale the physiological data. The system may also include a user interface configured to receive an input patient age of the patient and wherein the processor is further configured to at least one of scale and regulate the physiological data based on the apparent patient age and the input patient age.

In accordance with yet another aspect of the disclosure, a method for age-compensated monitoring of a patient experiencing an administration of at least one drug having anesthetic properties is provided. The method includes acquiring scout data from the plurality of sensors, and determining, from the scout data, a scale at least consistent with a patient age. The method also includes regulating acquisition of the physiological data based on the scale, and generating a report including the physiological data associated with the scale. In some aspects, determining the scale includes identifying age-correlated signal markers from the scout data and selecting the scale from a plurality of scales based on the age-correlated signal markers, and regulating acquisition of the physiological data comprises adjusting at least one amplifier gain based on the scale.

In accordance with yet another aspect of the disclosure, a system for age-compensated monitoring of a patient experiencing an administration of at least one drug having anesthetic properties is provided. The system includes a plurality of sensors configured to acquire physiological data from the patient, and a user interface configured to receive an indication of at least one of a characteristic of the patient. The system also includes a processor configured to determine, from at least the indication of at least one of a characteristic of the patient, a likely patient age, and select a scale based on the likely patient age. The system further includes a display configured to display the physiological data against the scale. In some aspects, the processor is further configured to determine, from the physiological data, an apparent patient age and select the scale based on the apparent patient age and the likely age, and perform a multitaper process to account for a dynamic range of signals spanning several orders of magnitude to format the physiological data to be displayed against the scale.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The present invention will hereafter be described with reference to the accompanying drawings, wherein like reference numerals denote like elements.

DETAILED DESCRIPTION

Figure 1A:
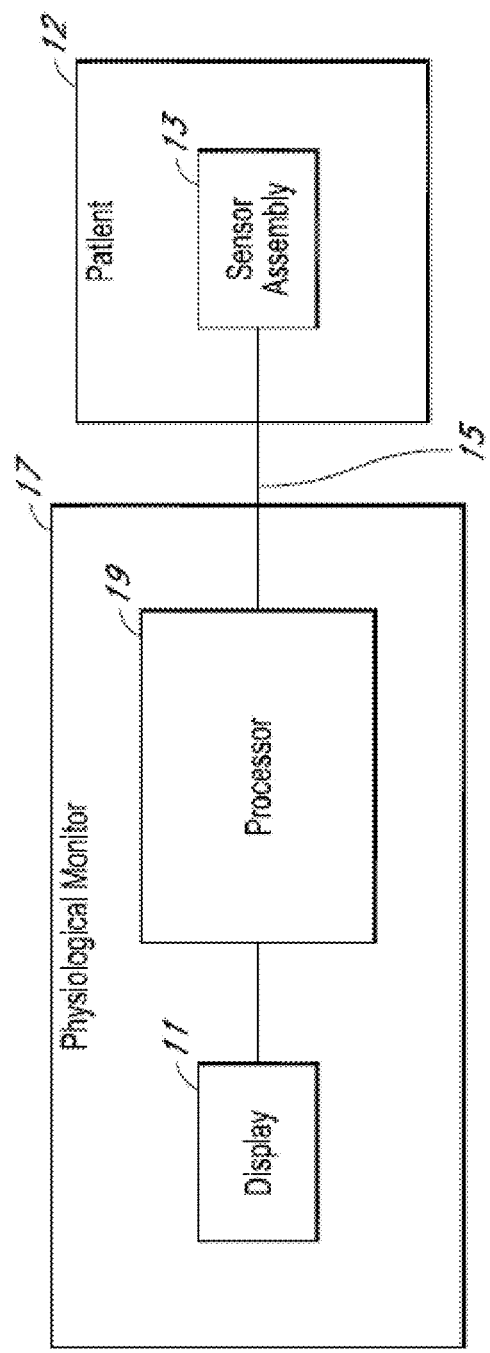
FIG. 1A is schematic block diagram of an example physiological monitoring system, in accordance with aspects of the present disclosure.

In the United States, nearly 60,000 patients receive general anesthesia per day to safely undergo surgical procedures, a large fraction of which are elderly, 60 years of age or older. Unlike treatment younger patients, anesthetic management of older patients requires additional care and carries higher risks. For example, the doses of anesthetics required to achieve the same level of general anesthesia in the elderly can range from 10 to 50 percent less than those required for younger patients. Also, increases in heart rate and decreases in blood pressure are more likely with older patients following induction of general anesthesia by bolus administration of a hypnotic, and measures are routinely taken to prevent the consequences of these expected changes.

Post-operative conditions in the elderly following general anesthesia and sedation are also a growing concern. For instance, delirium is an acute form of dysfunction whose symptoms include disorientation, impairment of attention and memory, while post-operative cognitive dysfunction ("POCD") is a persistent cognitive disorder that lasts from a few hours to several days or months. Specifically, POCD can range from difficulty with fact-finding and memory impairment to dementia and Alzheimer's-like symptoms. In addition, the prevalence of more subtle forms of POCD, which may go undetected without formal neuropsychological testing, may be greater than currently appreciated. Although it is presently unclear as to what degree anesthesia and sedation influence such conditions, as population ages, the fraction of the elderly patients who will require therapeutic and diagnostic procedures will continue to increase.

Changes in the brain's gross anatomy, associated with normal aging, have been demonstrated by prominent loss of volume and thickness in the prefrontal cortex, particularly in the dorsal medial and dorsal lateral prefrontal cortices, as well as the lateral parietal and lateral temporal cortices. Such loss of volume and thickness in the prefrontal cortical regions, which play prominent roles in attention and executive function, is consistent with the findings from numerous psychological experiments showing age-related decreases in performance on tests of attention and executive function. Prominent changes that have been reported in the viscerosensory region of the caudal insular cortex also appear to undergo relatively prominent thinning with normal aging. Other studies, regarding whether there is loss of thickness or volume in other brain regions, such as the primary sensory and motor cortices, paralimbic and limbic areas, hippocampus and entorhinal cortex, and the cingulate and insula, have provided mixed results.

In one study, young and middle-aged patients showed cortical thinning to be greatest in heteromodal associative cortices and in regions of high postnatal surface expansion. This is consistent with the idea that areas that had the greatest postnatal development show the greatest level of thinning, that is, the first-in-first-out hypothesis. However, it was found that cortical thinning in individuals 80 years and older was greatest in the primary sensory/motor cortices and regions of low postnatal surface area expansion. As a consequence, those investigators postulated that different factors affect cortical vulnerability as a function of age. Early on, developmental factors may confer vulnerability, whereas late in life factors specific to the primary sensory and motor cortices confer vulnerability.

Another group compared two independent samples of adult individuals who were cognitively normal when scanned at baseline. In one sample, 25 of the individuals were cognitively normal on follow-up and seven were Alzheimer's disease converters after an average follow-up of 11.1 years. In the second sample, 25 cognitively normal individuals were compared with seven Alzheimer's disease converters with an average follow-up of 7.1 years. The Alzheimer's disease converter individuals in both groups could be readily distinguished from the cognitively normal individuals by a small but consistent decrease in cortical thinning measured in nine pre-specified areas of interest. Cognitively normal individuals with mild thinning at baseline were more likely to convert to Alzheimer's disease than those with thicker cortical areas. It was subsequently confirmed that using a cortical thickness MRI biomarker was a reliable predictor of the likelihood for patients to develop Alzheimer's disease. The findings suggested a way to distinguish a patient who is cognitively normal from the one who is at risk for Alzheimer's disease, and could be helpful in identifying the extent to which postoperative cognitive disorders are related to exposure to anesthetic agents and surgery, and susceptibility to cognitive decline due to evolving, yet preclinical, Alzheimer's disease symptoms.

Contrary to some beliefs, normal brain aging does not entail substantial neuronal loss and cell death, but rather appreciable changes in neuronal morphology, with decreases in neuronal volume not uniform throughout the neocortex. Most noticeable are morphological changes occurring in the prefrontal cortex and the hippocampus, where synapse changes and the dendritic arbors and dendritic spines of pyramidal neurons decrease appreciably in size and number. There is also loss in white matter and increase in ventricular size, however it is postulated that changes in cognitive function seem more tightly related to the synaptic changes rather than gray matter or white matter changes.

With normal aging, there is a decrease in the synthesis of the major brain neurotransmitters including acetylcholine, dopamine, serotonin and glutamate and also a decrease in the number of receptors for these neurotransmitters. Aside from presumed impairment of inter-neuronal communication in general, the mechanism through which decreases in neurotransmitter levels contribute to specific changes in brain function is not well characterized. Decreased monoaminergic neurotransmitter levels have been related to increased proclivity toward depression and a decline in motor function in the elderly. Also, decreases in acetylcholine levels have been associated with Alzheimer's disease, and use of anticholinergic drugs in the peri-operative period is associated with an increased incidence of post-operative delirium particularly in older patients. These associations underlie the rationale to develop anticholinesterase inhibitors as a therapy to Alzheimer's disease and the general recommendation to avoid anticholinergic drugs, if possible, in the perioperative period to reduce the incidence of delirium in older patients. Despite the long-standing hypothesis of anticholinergic medications playing a role in delirium, administration of the anticholinesterase drugs has not been established as an effective therapy.

The aging brain also has a diminished maintenance capacity, in that factors that act to preserve normal function decline and are less effective. For example, neuroprotection and neurogenesis are important features that decline with normal aging. In addition, the brain becomes more susceptible to factors that impair functions, such as oxidative stress and inflammation. Since the brain is especially susceptible to oxidative stress, consuming a higher fraction of oxygen relative to the other parts of the body, aggravated oxidative stress has been shown to increase with aging, while antioxidant activity decreases. As such, oxidative stress facilitates neuronal injury through modifications of DNA, proteins and lipids, leading to altered mitochondrial- and $Ca^{2+}$-mediated functions and an increase in reactive astrocytes. For example, the brain-derived neurotrophic factor is postulated to play an important role in neurogenesis, yet also has antioxidant and anti-inflammatory effects. Thus, decreased brain-derived neurotrophic factor activity in the hippocampus impairs stem cell activity in the nearby dentate gyrus. Similarly, telomeres, the DNA-protein complexes that protect DNA from damage, tend to shorten with age, as well as with processes that are genotoxic and cytotoxic. Given that neurons in the brain generally do not die or divide, cellular damage typically accumulates it with aging. Together these factors contribute to a decrease in plasticity with age.

In spite of greater understanding of the aging brain derived from functional imaging, neurophysiological and epidemiological studies, appreciably changes in management of elderly patients receiving anesthesia care have not taken place. Many long-standing edicts for managing elderly patients receiving general anesthesia and sedation have been reinforced by the findings from recent studies. For example, in one retrospective study, the same level of sedation during colonoscopies for elderly patients (3 years) was achieved as with younger patients by administering a significantly lower weight-adjusted and total dose of propofol. In another retrospective study of propofol use in the emergency room, elderly patients were found to require a lower induction dose relative to the young patients and a lower overall dose compared to both young and middle-aged patients. Also, it was shown that pretreatment with midazolam reduced the amount of propofol needed for the induction of general anesthesia and the hypo-tensive response to induction in patients 65 years and older. Furthermore, in a randomized controlled trial, it was found that using the bispectral index (BIS) to titrate anesthetic delivery reduced the anesthetic exposure, and hence the incidence of delirium in the immediate postoperative period and the likelihood of POCD three months following surgery.

In addition to brain changes due to normal brain aging, specific neurodegenerative disorders are also associated with specific anatomic features, such as the neurofibrillary tangles and amyloid plaques commonly related to Alzheimer's disease, and micro-vascular changes, associated with lacunar stroke, leukoaraiosis, vascular dementia as well as Alzheimer's disease. For example, recent studies have provided information in relation to postoperative outcomes of patients with preoperative cognitive impairments. In a double-blinded protocol, BIS values and time to extubation were compared in a cohort of patients with MCI and age-matched controls. The MCI patients required significantly lower induction doses of propofol and had significantly lower BIS scores before induction, immediately after induction and a few minutes following discontinuation of the propofol and remifentanil infusions. The investigators suggested that use of standard BIS target values for the general population did not apply to patients with MCI. Also, in a prospective study of delirium and POCD in patients undergoing coronary artery bypass surgery, nearly half of patients had postoperative delirium associated with a significantly lower Mini Mental State Examination ("MMSE") score compared to those who did not develop delirium. The patients with postoperative delirium had a significantly greater drop in MMSE than the non-delirium group, and this difference lasted for 30 days following surgery. Also, six months following surgery, a higher fraction of patients in the delirium group had not returned to their preoperative baseline. In addition, an in-vivo study suggested that desflurane may be less deleterious than isoflurane to Alzheimer's disease patients requiring anesthesia. Together, these studies suggest that patients with impaired cognitive function preoperatively may be at greater risk for cognitive dysfunction in the immediate post-operative period and that this dysfunction may persist for several months following the surgery.

Use of electroencephalogram ("EEG") recordings to monitor and diagnose cognitive states in elderly patients has been previously demonstrated. For example, in one study, cortical gray matter was analyzed both using magnetic resonance imaging ("MRI") and cortical EEG rhythms, in cognitively normal individuals, individuals with amnestic mild cognitive impairment ("MCI") and Alzheimer's patients. Relative to the cognitively normal individuals, the MCI individuals displayed a decrease in the alpha-1 rhythm (8-10.5 Hz) source. Compared with the cognitively normal and the MCI individuals, the Alzheimer's disease patients had a decrease in the amplitude of the alpha-1 rhythm source and an increase in the amplitude of the delta rhythm (2-4 Hz) source. Overall, for the MCI and Alzheimer's disease patients, lower cortical gray matter volume and poor performance on cognitive tests were associated with lower alpha-1 and higher delta sources, suggesting that resting-state EEG measurements may provide ways of diagnosing impaired cognitive states. Also, some studies showed that the brain states of patients under general anesthesia may be tracked using the unprocessed EEGs and corresponding spectrograms. In addition, it was shown that differences likely exist between the unprocessed EEGs and spectrograms of cognitively normal elderly, MCI and Alzheimer's disease patients under general anesthesia. Similarly, observations of patients in the operating room showed that there are differences in EEG measurements between young, middle-aged and elderly patients under general anesthesia.

Similarly, there is growing concern that anesthetic exposure in children could result in significant lasting changes in brain function or development, including neurodegeneration. Presently, existing EEG-based anesthetic brain monitors are not approved for use in children. The ongoing development of brain circuits throughout childhood suggest that anesthesia-induced EEG signals could take different forms compared to their adult counterparts, which in turn suggests that adult monitors might misinterpret anesthesia-induced EEG signals in children. Establishing the correct dose of anesthetic drugs in pediatric patients is a high priority in order to limit the potentially damaging effects of anesthetic exposure.

Therefore, considering the above, there continues to be a clear need for systems and methods that take into account information related to brain age, development, and function for monitoring patients undergoing medical procedures.

The present disclosure, in recognizing the need for accurate and appropriate brain monitoring not found in previous technologies, provides systems and methods directed to determining and using patient-specific from brain signals. For example, age-related information may be determined or inferred. As will become apparent, systems and methods described herein may be particularly beneficial for applications associated with medical procedures, including general anesthesia and sedation. For example, such approaches may be used to pre-operatively identify patients potentially at higher risk for post-operative cognitive conditions or disorders. In addition, age-related information may be used to give certain age-appropriate indications or treatments, such as specific regimens for anesthetic, post-anesthetic, or intensive care.

As will be described, a number of approaches are provided describing how patient-specific information, such as an apparent or likely patient age information, could be used to improve brain monitoring during anesthesia or sedation using systems and methods provided. For example, given a patient age, the most appropriate EEG signatures could be utilized, specified in terms of spectrum and/or coherence, for example, to infer the level of anesthesia or sedation. Specifically, in very young children less than one year old, the EEG spectrum and coherence in the anesthetized state show a different form compared to older children or adults. In this instance, the characteristic spectrum and coherence for this age group could be used to infer when patients are anesthetized. In another example, in older children and in adults, knowledge of the patient's age could be used to establish the most appropriate scale to use for displaying the EEG or processed EEG such as the spectrogram.

As will be described, in one mode of operation, systems in accordance with this disclosure could use a patient's age to select the most appropriate age-dependent EEG signatures, specified in terms of spectrum and/or coherence, for example, to infer the level of anesthesia or sedation for that patient. In another mode of operation, the systems as described could be configured to analyze a patient's EEG, and use it to infer that patient's apparent age or brain age. In yet another mode of operation, the present invention could use both the patient's age as well as the patient's EEG to both infer the patient's apparent age or brain age, and to select the most appropriate age-dependent EEG signatures to infer the level of anesthesia or sedation for that patient. These different modes of operation would employ a quantitative or computational representation of the relationship between anesthesia-induced EEG patterns, different brain states or states of consciousness, and age. This quantitative or computational representation could take the form of reference databases, or listings, to include mathematical or statistical models relating EEG patterns and age.

Figure 1B:
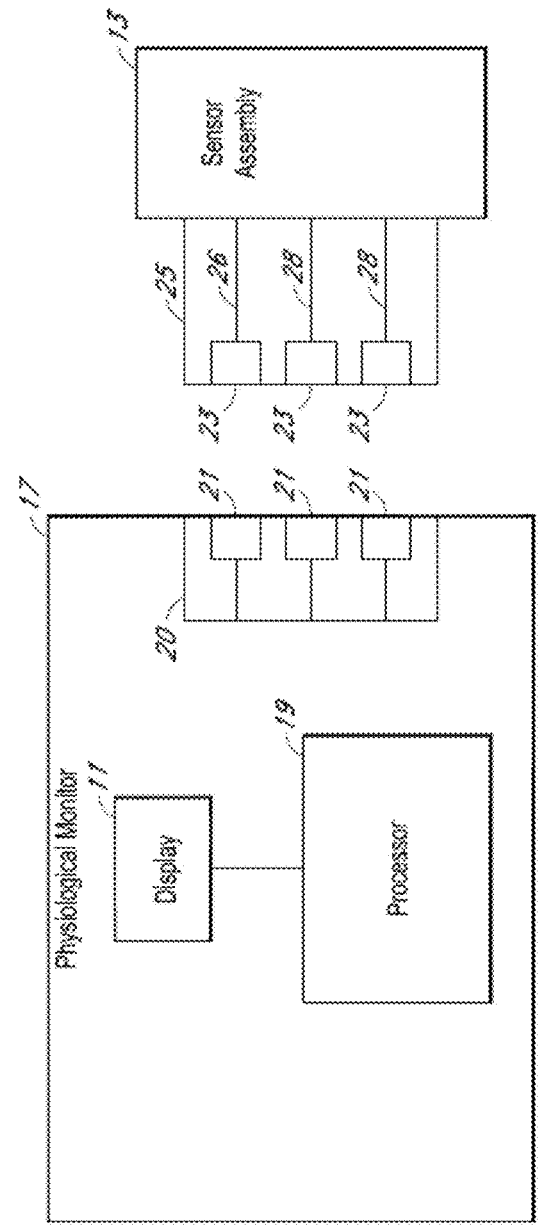
FIG. 1B is schematic block diagram of another example physiological monitoring systems, in accordance with aspects of the present disclosure.

Referring now to the drawings, FIGS. 1A and 1B illustrate example patient monitoring systems and sensors that can be used to provide physiological monitoring of a patient, such as age-compensated monitoring of a patient experiencing an administration of at least one drug having anesthetic properties.

For example, FIG. 1A shows an embodiment of a physiological monitoring system 10. In the physiological monitoring system 10, a medical patient 12 is monitored using one or more sensors 13, each of which transmits a signal over a cable 15 or other communication link or medium to a physiological monitor 17. The physiological monitor 17 includes a processor 19 and, optionally, a display 11. The one or more sensors 13 include sensing elements such as, for example, electrical EEG sensors, or the like. The sensors 13 can generate respective signals by measuring a physiological parameter of the patient 12. The signals are then processed by one or more processors 19. The one or more processors 19 then communicate the processed signal to the display 11 if a display 11 is provided. In an embodiment, the display 11 is incorporated in the physiological monitor 17. In another embodiment, the display 11 is separate from the physiological monitor 17. The monitoring system 10 is a portable monitoring system in one configuration. In another instance, the monitoring system 10 is a pod, without a display, and is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two EEG sensors. In still another embodiment, the one or more sensors 13 include at least two EEG sensors and one or more brain oxygenation sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the EEG sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors, one or more additional cables 15 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

In some configurations, systems shown in FIGS. 1A and 1B may further include a memory, database or other data storage locations (not shown), accessible by processor 19, to include reference information or other data. Specifically, such reference information can include reference listings, look-up tables, and models, including patient categories, such as various age categories, and other categories, along with associated signals, signal markers or signatures. For example, signal markers or signatures can include various signal amplitudes, phases, frequencies, power spectra, spectrograms, coherograms, and so forth. In some aspects, such reference information can be used by the processor 19, optionally including user input or selections, to determine specific patient characteristics, such an apparent or likely patient age, or other patient conditions or categories. Specifically, a processor 19 may process and analyze acquired data to determine signal markers or signatures, using various analysis methods, including waveform analyses, spectral analyses, frequency analyses, coherence analyses and so on. Subsequently, patient characteristics may be identified by performing a comparison of the determined signal markers or signatures with those categorized in the reference, thus identifying a patient category closely resembling the patient-specific information. For example, a spectrogram or coherogram generated from the acquired data by the processor 19 may then be compared to a listing of spectrograms or coherograms to identify specific patient categories, related to patient characteristics, such as an apparent or likely patient age, or age range. In addition, inferences regarding patient characteristics can be performed by the processor 19 using regression or statistical models, perhaps employing Bayesian inference to jointly incorporate age and EEG-related information, machine learning methods, or through cross-correlation, clustering, or related techniques.

In some aspects of the disclosure, the reference information may include pertinent covariate information for interpreting the EEG and age information, including patient variables and history such as height, weight, or gender, as well as information about the drugs administered to the patient, their doses and timing. The assessment of apparent age could be related or represented in terms of numerical age, but could also be represented in terms of neurological or cognitive conditions related to age, such as developmental stages in children, or age-related conditions such as cognitive impairment, dementia, or Alzheimer's disease, for instance. The representation of the EEG in the database or model could be made in any number of ways, including frequency-dependent measures such as spectrum, coherence, spectrogram, or cohereogram, time-domain measures such as amplitude or morphology, or other measures such as cross-frequency coupling, for instance. Inferences from the database or model could be made using any number of appropriate established methods, including look-up tables, prediction using a regression or statistical model, perhaps employing Bayesian inference to jointly incorporate age and EEG-related information, machine learning methods, or through cross-correlation, clustering, or related techniques.

In some embodiments, a data acquisition process may be regulated or modified based on selected and/or determined patient characteristics. For example, the processor 19 may be configured to determine and apply an appropriate scale during data acquisition using the patient characteristics, such as an apparent or likely patient age, identified in scout data. In other embodiments, a display of acquired physiological data may be modified based on determined patient characteristics. Specifically, the data may be displayed against a scale determined by processor 19. In some aspects, scale may be displayed using a numerical scale, a color scale, a gray scale, or combinations thereof.

Figure 2:
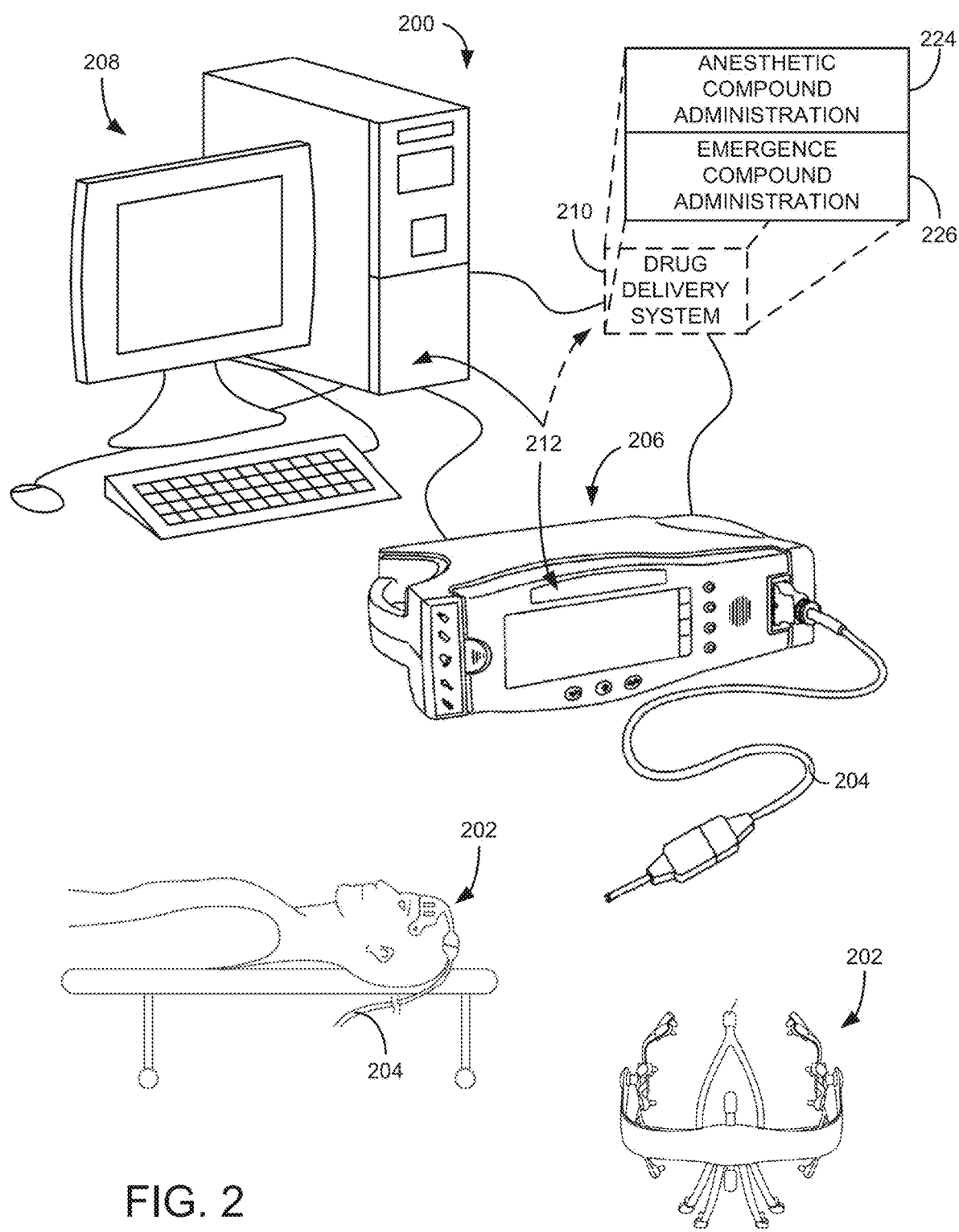
FIG. 2 is an illustration of an example monitoring and control system, in accordance with aspects of the present disclosure.

Specifically now referring to FIG. 2, an exemplary system 200 in accordance with aspects of the present disclosure is illustrated, which may be constructed as a stand-alone brain monitoring device, or portable device, or could be incorporated as a central component of an existing brain monitoring device. As will be appreciated from forthcoming descriptions, the system 200 may find valuable usage within an operating room or an intensive care setting, in association with conducting a variety of medical procedures, such as during administration of an anesthetic, as well as within a pre- or post-operative evaluation situation.

The system 200 includes a patient monitoring device 202, such as a physiological monitoring device, illustrated in FIG. 2 as an electroencephalography (EEG) electrode array. However, it is contemplated that the patient monitoring device 202 may include a number of different sensors. In particular, the patient monitoring device 202 may also include mechanisms for monitoring galvanic skin response (GSR), for example, to measure arousal to external stimuli or other monitoring system such as cardiovascular monitors, including electrocardiographic and blood pressure monitors, and also ocular microtremor monitors. One realization of this design may utilize a frontal Laplacian EEG electrode layout with additional electrodes to measure GSR and/or ocular microtremor. Another realization of this design may incorporate a frontal array of electrodes that could be combined in post-processing to obtain any combination of electrodes found to optimally detect the EEG signatures described earlier, also with separate GSR electrodes. Another realization of this design may utilize a high-density layout sampling the entire scalp surface using between 64 to 256 sensors for the purpose of source localization, also with separate GSR electrodes.

The patient monitoring device 202 is connected via a cable 204 to communicate with a monitoring system 206. Also, the cable 204 and similar connections can be replaced by wireless connections between components. The monitoring system 206 may be configured to receive raw signals from patient monitoring device 202, such as signals acquired by the EEG electrode array, and assemble, process, and even display the signals in various forms, including time-series waveforms, spectrograms, and the like. In some modes of operation, the monitoring system 206 may be designed to acquire scout data, in the form of physiological or other data, from sensors on the patient monitoring device 202 and identify, using the scout data, signal markers, or signatures therein. For example, signal amplitudes, phases, frequencies, power spectra, and other signal markers or signatures, may be identified in scout data, and other acquired data, using various suitable methods. In addition, a multitaper analysis may be performed to identify and account for a dynamic range of signals spanning several orders of magnitude. Such signal markers or signature may then be used by the monitoring system 206 to determine various patient characteristics, including an apparent and/or likely patient age.

In one embodiment, acquisition of physiological data using monitoring system 206 may be adjusted or regulated based patient characteristics determined from scout data. Specifically, the monitoring system 206 may be configured to determine a scale consistent with certain determined patient characteristics, and adjust subsequent data acquisition, based on the determined scale and/or any indication provided by user. For instance, data acquisition may be regulated by adjusting one or more amplifier gains, along with other data acquisition parameters. Moreover, in some aspects, the monitoring system 206 may be further configured to format various acquired physiological data to be displayed against the scale. In this manner, an age-appropriate scale may be determined based on the apparent and/or likely patient age, and any subsequent data acquisition using a selected age-appropriate scale would generate and illustrate age-compensated data.

As illustrated, the monitoring system 206 may be further connected to a dedicated analysis system 208. However, the monitoring system 206 and analysis system 208 may be integrated or combined into a common system. The analysis system 208 may receive EEG waveforms from the monitoring system 206 and, as will be described, analyze the EEG waveforms and signatures therein. However, it is also contemplated that any analysis or processing functions of the monitoring system 206 and analysis system 208 may be shared or individually distributed, as required or desired.

In some aspects, information related to determined characteristics of a patient undergoing a specific medical procedure may be provided to a clinician or operator of system 200. For example, it was previously found that elderly patients were more likely to enter burst suppression in the operating room. Specifically, burst suppression is the profound state of brain inactivation in which bursts of electrical activity are interspersed with isoelectric periods termed suppressions. Brain states of anesthetic-induced unconsciousness, defined by the alpha wave (8-10 Hz) and slow wave (0.1-4 Hz) signal oscillations, can be obtained with doses of anesthetics that are less than those required to produce burst suppression. This may mean reducing anesthetic dosing to levels substantially less than what are currently recommended for elderly individuals. Because currently recommended doses typically place elderly patients into burst suppression, adequate states of general anesthesia and reduced anesthetic exposure may be achievable by titrating anesthetic dosing based on real-time EEG monitoring. Hence system 200 may provide, based on determined patient characteristics, information for use in selecting an appropriate anesthetic dosing. In this manner, for example, incidence of post-operative cognitive disorders for elderly patients under general anesthesia may be reduced.

In another example, monitoring system 206 and/or analysis system 208 may be capable of providing a pre- or post-operative assessment of specific patients, such as the young, middle-aged and elderly, as well as drug addicted patients, to determine prior information that could be used to identify and/or predict specific patient conditions, including anesthetic sensitivity, and any potential for post-operative complications, such as cognitive disorders. Moreover, specific regimens for anesthetic care, post-anesthesia care, or intensive care, may also be provided.

The system 200 may also include a drug delivery system 210. The drug delivery system 210 may be coupled to the analysis system 208 and monitoring system 208, such that the system 200 forms a closed-loop monitoring and control system. Such a closed-loop monitoring and control system in accordance with the present disclosure is capable of a wide range of operation, but includes user interfaces 212 to allow a user to configure the closed-loop monitoring and control system, receive feedback from the closed-loop monitoring and control system, and, if needed reconfigure and/or override the closed-loop monitoring and control system. In some configurations, the drug delivery system 210 is not only able to control the administration of anesthetic compounds for the purpose of placing the patient in a state of reduced consciousness influenced by the anesthetic compounds, such as general anesthesia or sedation, but can also implement and reflect systems and methods for bringing a patient to and from a state of greater or lesser consciousness.

For example, in accordance with one aspect of the present invention, methylphenidate (MPH) can be used as an inhibitor of dopamine and norepinephrine reuptake transporters and actively induces emergence from isoflurane general anesthesia. MPH can be used to restore consciousness, induce electroencephalogram changes consistent with arousal, and increase respiratory drive. The behavioral and respiratory effects induced by methylphenidate can be inhibited by droperidol, supporting the evidence that methylphenidate induces arousal by activating a dopaminergic arousal pathway. Plethysmography and blood gas experiments establish that methylphenidate increases minute ventilation, which increases the rate of anesthetic elimination from the brain. Also, ethylphenidate or other agents can be used to actively induce emergence from isoflurane, propofol, or other general anesthesia by increasing arousal using a control system, such as described above.

Therefore, a system, such as described above with respect to FIG. 2, can be provided to carry out active emergence from anesthesia by including a drug delivery system 210 with two specific sub-systems. As such, the drug delivery system 210 may include an anesthetic compound administration system 224 that is designed to deliver doses of one or more anesthetic compounds to a subject and may also include a emergence compound administration system 226 that is designed to deliver doses of one or more compounds that will reverse general anesthesia or the enhance the natural emergence of a subject from anesthesia.

For example, MPH and analogues and derivatives thereof induces emergence of a subject from anesthesia-induced unconsciousness by increasing arousal and respiratory drive. Thus, the emergence compound administration system 326 can be used to deliver MPH, amphetamine, modafinil, amantadine, or caffeine to reverse general anesthetic-induced unconsciousness and respiratory depression at the end of surgery. The MPH may be dextro-methylphenidate (D-MPH), racemic methylphenidate, or leva-methylphenidate (L-MPH), or may be compositions in equal or different ratios, such as about 50 percent:50 percent, or about 60 percent:40 percent, or about 70 percent:30 percent, or 80 percent:20 percent, 90 percent:10 percent, 95 percent:5 percent and the like. Other agents may be administered as a higher dose of methylphenidate than the dose used for the treatment of Attention Deficit Disorder (ADD) or Attention Deficit Hyperactivity Disorder (ADHD), such as a dose of methylphenidate can be between about 10 mg/kg and about 5 mg/kg, and any integer between about 5 mg/kg and 10 mg/kg. In some situations, the dose is between about 7 mg/kg and about 0.1 mg/kg, or between about 5 mg/kg and about 0.5 mg/kg. Other agents may include those that are inhaled.

Figure 3:
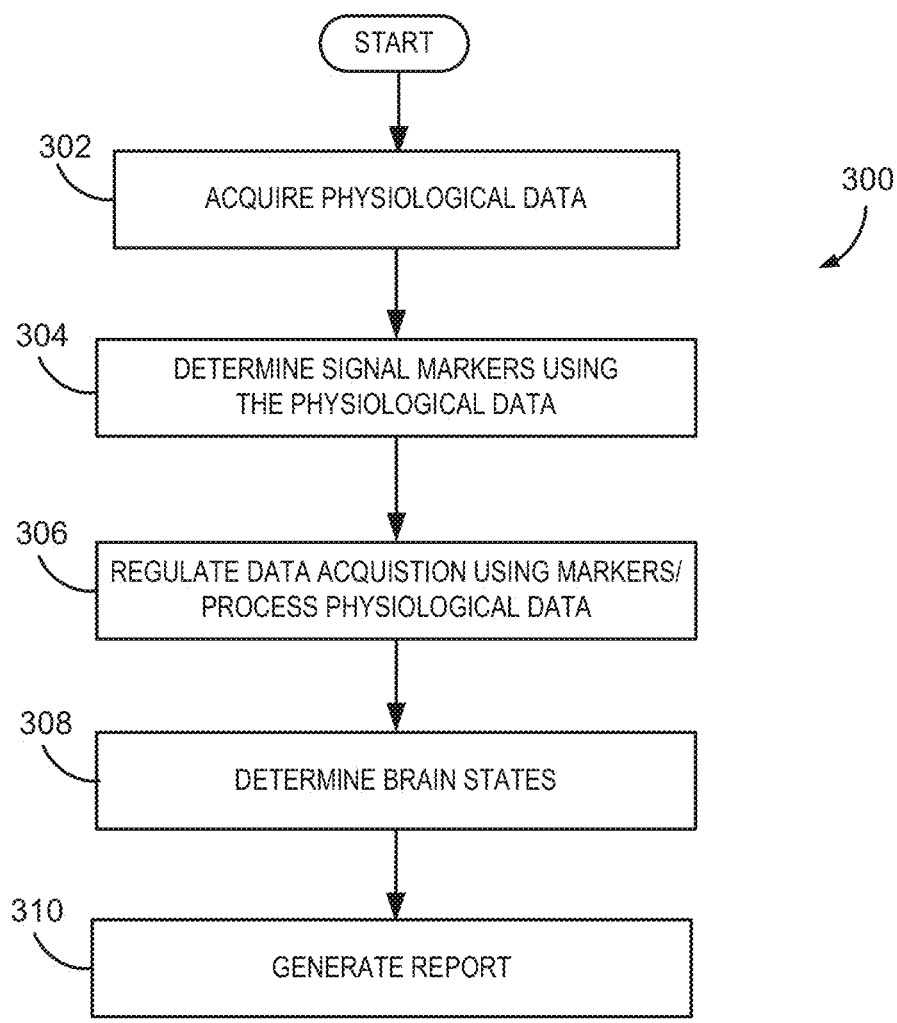
FIG. 3 is a flowchart illustrating the process steps associated with a mode of operation for a monitoring system, in accordance with the present disclosure.

Turning to FIG. 3, process 300 in accordance with aspects of the present disclosure is shown. Beginning with process block 302, any amount of physiological data may be acquired, wherein the physiological data is representative of physiological signals, such as EEG signals, obtained from a patient using, for example, the patient monitoring device 202. In some aspects, the physiological data may include scout data for purposes including determining various patient characteristics. Then at process block 304, signal markers or signatures are identified or determined using the acquired physiological data. For example, signal amplitudes, phases, frequencies, power spectra, and other signal markers or signatures, may be identified in scout data, and/or other acquired data, using various suitable methods.

In some preferred embodiments, the signal markers or signatures may be used to determine patient characteristics, including an apparent and/or likely patient age. In addition, process block 304 may also include steps of determining a scale consistent with determined patient characteristics. In one aspect, use of spectral estimation methods, such as the multi-taper method, that can inherently account for a wide dynamic range of signals spanning many orders of magnitude may be employed. In another aspect, an automatic estimation of signal amplitudes may be performed to infer a correct age cohort and attendant settings for a visualization scale, as well as for acquisition amplifier gains.

At the next process block 306, using the signal markers or signatures determined from the scout data, a data acquisition process may be adjusted or regulated, in relation to signal data to be acquired subsequently. For instance, data acquisition may be regulated by adjusting one or more amplifier gains, along with other data acquisition parameters. In some aspects, regulating data acquisition may also include determining and using a scale consistent with determined patient characteristics, and adjusting a subsequent data acquisition process based on the determined scale and/or any indication provided by user. By way of example, an age-appropriate scale determined at process block 304, based on the apparent and/or likely patient age, may be used, and any subsequent data acquisition using a selected age-appropriate scale would generate age-compensated data. In other aspects, a display of physiological data acquired at process block 302 may be modified using the scale. Such scale may be displayed using a numerical scale, a color scale, a gray scale, or combinations thereof.

At process block 308, data acquired in a manner described may be used to determine current or future brain states of patient. For example, analyzed or processed EEG waveforms assembled using age-compensated data may be used to assess a present and/or future depth of anesthesia or sedation. In addition, determining such brain states may also include any information provided by a clinician or user, such as information related to a medical procedure.

Figure 4A:
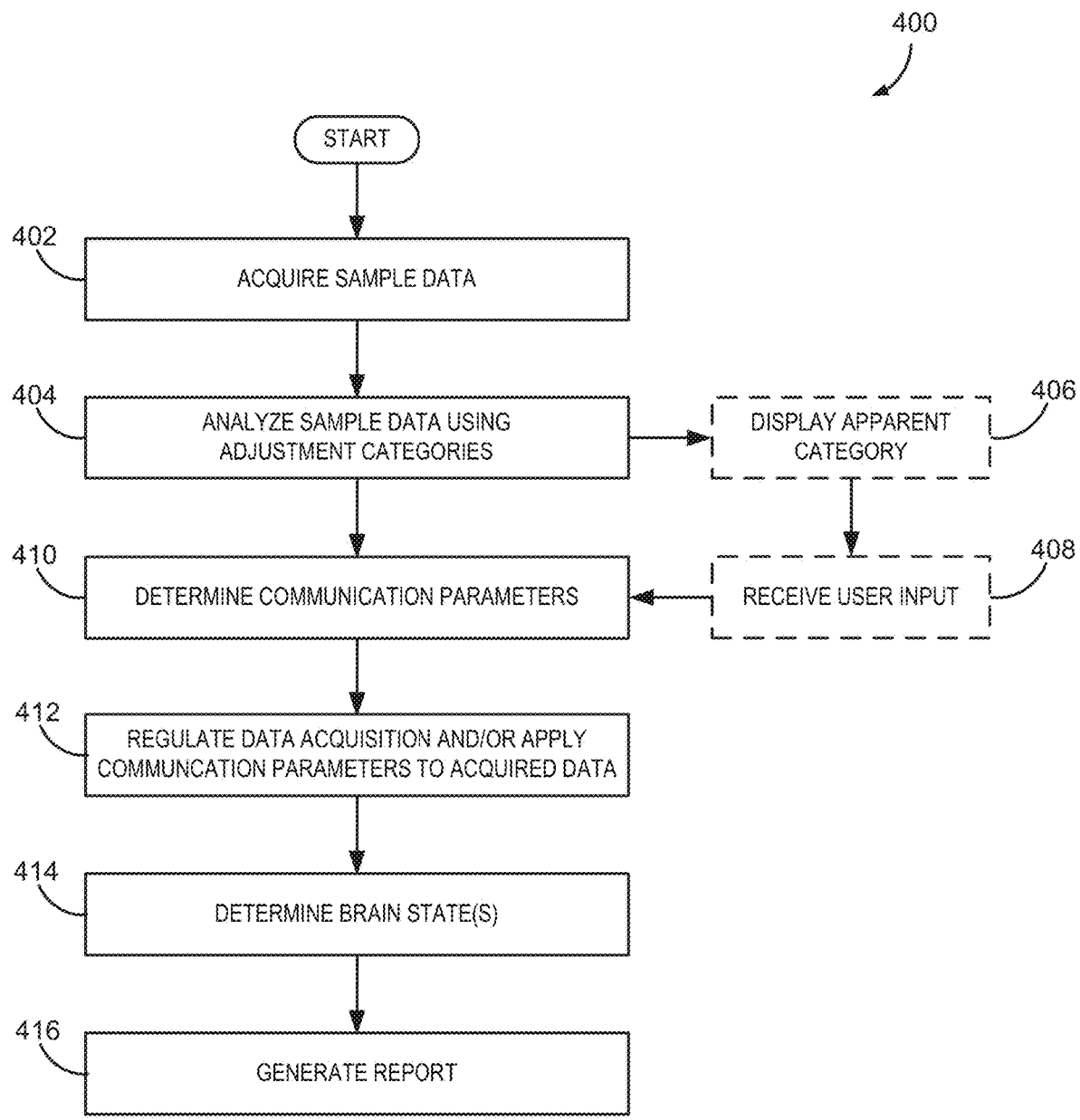
FIG. 4A is a flowchart illustrating the process steps associated with another mode of operation for a monitoring system, in accordance with the present disclosure.

Then at process block 310 a report is generated, for example, in the form a printed report or, preferably, a real-time display. The report may include raw or processed data, signature information, indications of current or future brain states, as well as information related to patient-specific characteristics, including as a likely and/or apparent patient age. Displayed signature information or determined states may be in the form of a waveforms, spectrograms, coherograms, probability curves and so forth. In some aspects, the report may include formatted physiological data displayed against a scale. In other aspects, the report may indicate an anesthetic sensitivity, a probability for post-operative complications, such as cognitive disorders, and also regimens for anesthetic care, post-anesthesia care, or intensive care, and so forth Turning to FIG. 4A, steps of another process 400 in accordance with aspects of the present disclosure are illustrated. Specifically, the process 400 begins at process block 402 where sample or scout data is acquired using, for example, patient monitoring systems, as described. At process block 404, the sample data is then analyzed using various adjustment or reference categories, to identify patient categories representative of the acquired sample data. Specifically, this step includes identifying signal markers or signatures in the sample data and performing a comparison with signal markers or signatures associated with the reference categories. For example, signal amplitudes, phases, frequencies, power spectra, and other signal markers or signatures, can be detected in the sample data using various suitable methods.

Analysis, as performed at process block 404, can indicate specific patient characteristics, including an apparent and/or likely patient age. In some aspects, an identified or apparent category indicating specific patient characteristics may be optionally displayed at process block 406. Moreover, at process block 408 a user input may also be received.

Subsequently, at process block 410 a determination is made with respect to various communication parameters. This includes taking into consideration determined or inferred patient characteristics or categories, and optionally a user input. For example, an age-appropriate scale for the acquired data may be determined at process block 410 based on determined patient characteristics and/or signals, signal markers or signatures present in the acquired data. Then at process block 412, a subsequent data acquisition may be regulated using the determined communication parameters to acquire age-appropriate data. As described, regulating data acquisition may include appropriately adjusting or modifying various amplifier gains using the communication parameters. In some aspects, the determined communication parameters may be directly applied to the acquired sample data. For example, an age-appropriate scale may be applied to the sample data to create age-appropriate or compensated data.

Then, at process block 414, data acquired or processed in a manner described may be used to determine current or future brain states of patient. For example, analyzed or processed EEG waveforms assembled using age-compensated data may be used to assess a present and/or future depth of anesthesia or sedation. In addition, determining such brain states may also include any information provided by a clinician or user, such as information related to a medical procedure.

Then at process block 416 a report is generated of any suitable shape or form. In some aspects, the report may be a display scaled data or data categories describing the data. In other aspects, the report may indicate an anesthetic sensitivity, a probability for operative or post-operative complications, an apparent or likely patient age, and other information related to aspects of the present disclosure.

Figure 4B:
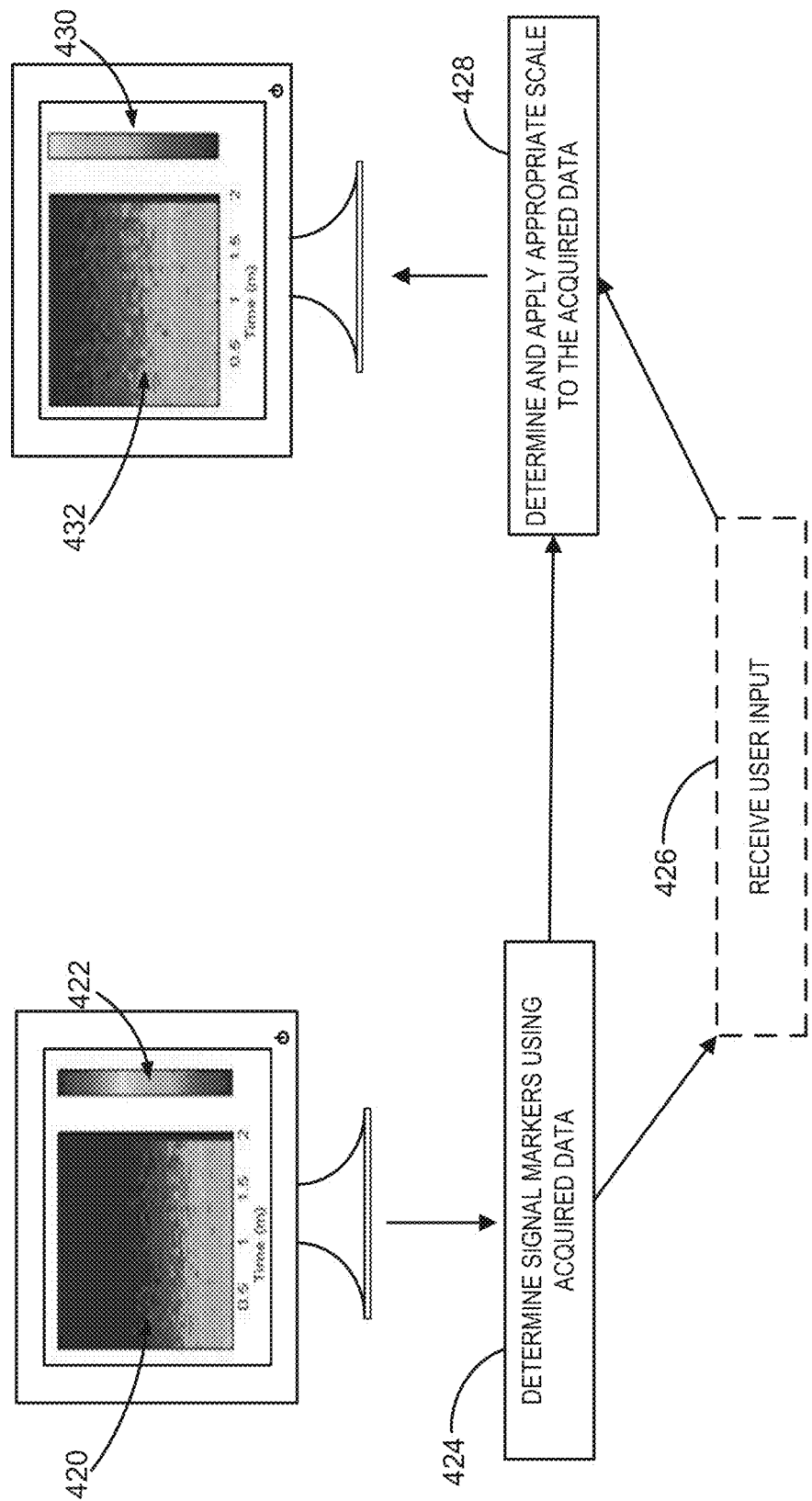
FIG. 4B is a schematic diagram illustrating steps in accordance with aspects of the present disclosure.

Turning to FIG. 4B a schematic diagram illustrating steps in accordance with one embodiment of the present invention is shown. Specifically, acquired data 420, optionally processed and displayed using a raw scale 422, may be used to determine signal markers or signatures at step 424. As described, this step includes a number of processing or analysis steps, including waveform analyses, spectral analyses, frequency analyses, coherence analyses and so on. Then at step 428 information related to the determined signal markers or signatures may be determined. Particularly, patient characteristics may be identified by performing a comparison of the determined signal markers or signatures with those categorized in a reference, thus identifying a most similar patient category. For example, an apparent or likely age may be identified.

In this manner, using information identified in the acquired data 420, an appropriate scale 430 for the acquired data 420 may be determined and/or selected at step 428 and applied to the acquired data to generate and display modified or scaled data 432. For example, a determined apparent or likely patient age, or age range, may be used to identify an age-appropriate scale, and generate age-compensated data, which may be optionally displayed. In some aspects, this step may also include receiving a user input at step 426. For example, a clinician may provide information relevant to a monitored patient, including a patient's real age, as well as information related to a medical procedure, such as a specific anesthetic or dose. In some aspects, the modified data 432, appropriately scaled and/or displayed, may then be utilized in a brain analysis process to correctly identify brain states of the patient.

Figure 4C:
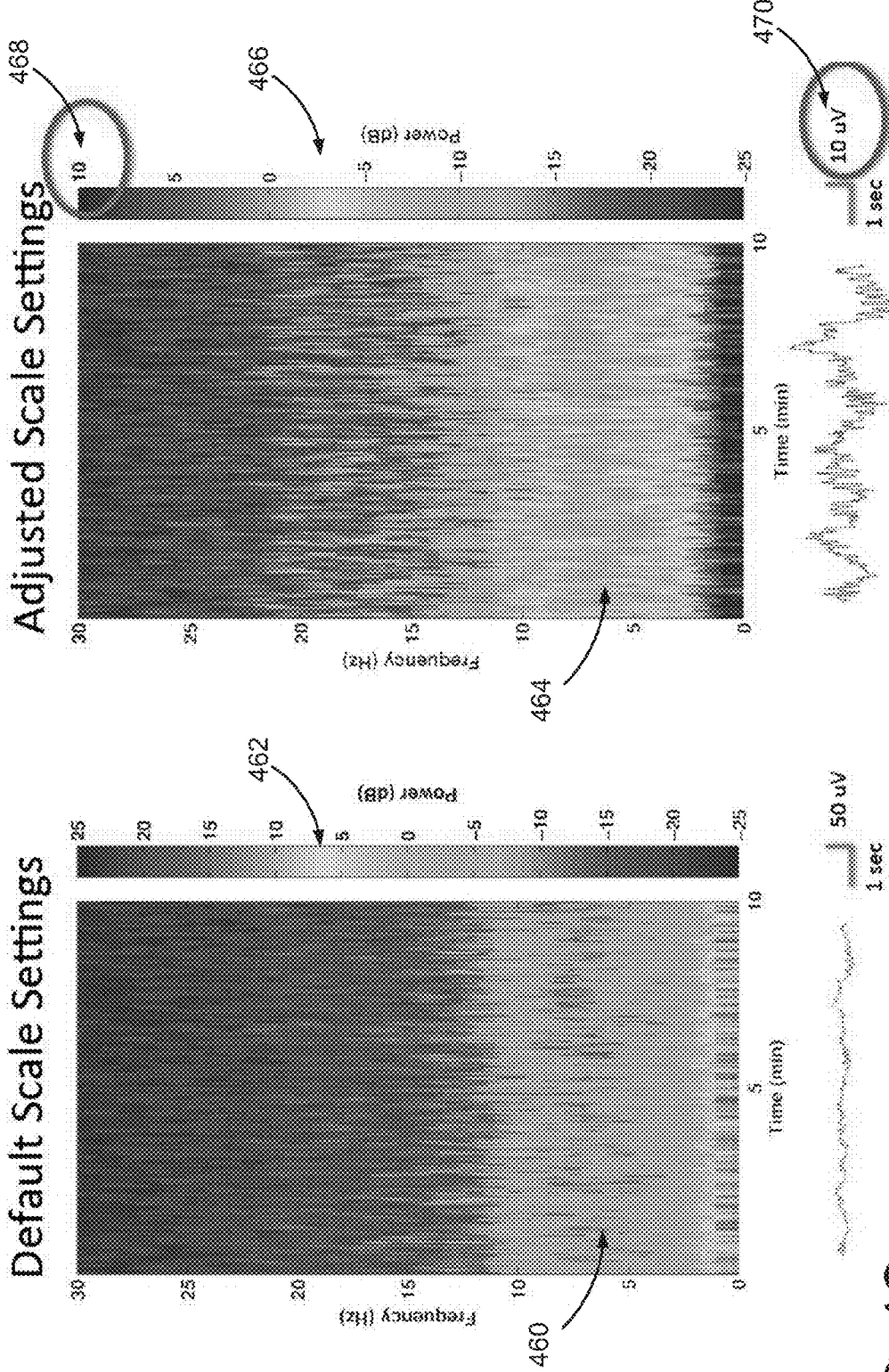
FIG. 4C shows an example scale adjustment in accordance with aspects of the present disclosure.

By way of example, FIG. 4C shows an example scale adjustment for a 61 year old patient, in accordance with aspects of the present disclosure. Specifically, acquired spectrogram data 460 is displayed using a default scale 462 setting, which may not be ideal or appropriate. Following steps as described to identify an apparent or likely patient age, scaled data 464 is generated and displayed against an appropriate scale 466 determined using identified patient characteristics. Specifically, the power limits 468 of the appropriate scale 466, and the amplitude limits 470 for an amplitude scale, for a representative time-domain EEG trace data, are adjusted based on age. By adjusting the scale, the resulting display more clearly represents the frequency structure and time-domain morphology of the EEG signal, enabling accurate visualization and assessment of the patient's state of anesthesia or sedation.

Figure 4D:
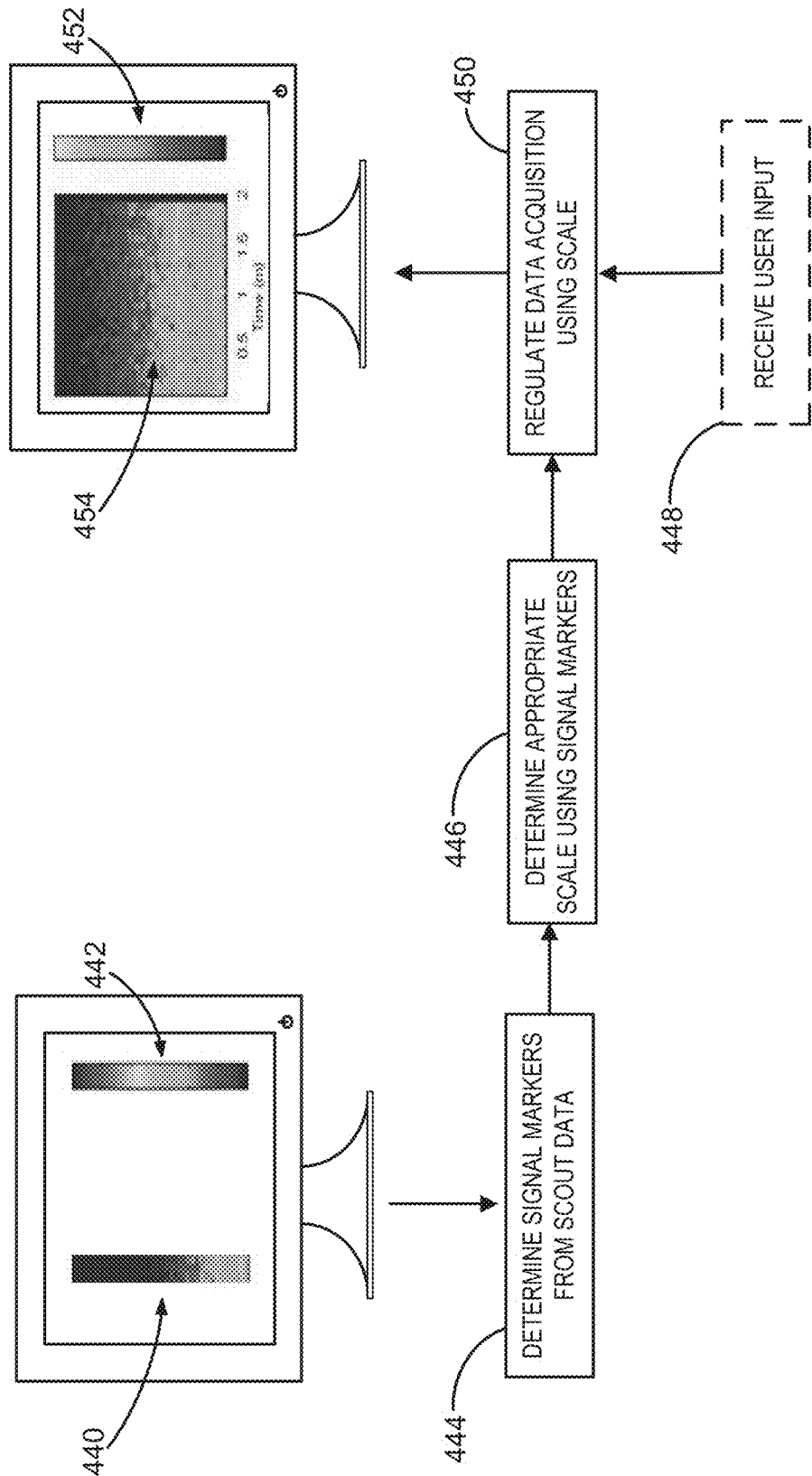
FIG. 4D is a schematic diagram illustrating steps in accordance with aspects of the present disclosure.

Turning to FIG. 4D a schematic diagram illustrating steps in accordance with another embodiment of the present invention is shown. Particularly scout data 440, optionally displayed against a raw scale 442, may be utilized at step 444 to determine signal markers present in the scout data 440, using analyses as described. At step 446 an appropriate or compensated scale 452, which may different than a default setting, is determined using signal markers and other information determined from the scout data 440. Optionally other parameters may also be determined at step 446 from the scout data 400, including a number of data acquisition parameters. For example, appropriate amplifier gains may also be identified via dynamic range exhibited by the scout data.

At step 450 a data acquisition process 450 may be regulated or modified using the appropriate scale 452 in order to generate appropriate data 454. Optionally, this step may include input 448 received from a user. For example, a clinician may provide information relevant to a monitored patient, including a patient's real age, as well as information related to a medical procedure, such as a specific anesthetic or dose. Additionally, a user input may include selection of acquisition parameters, over-riding instructions, or other input related to the data acquisition process. In some aspects, the appropriate data 454, suitably acquired and/or displayed using patient-specific characteristics, may then be utilized in a brain analysis process to correctly identify brain states of the patient.

Examples of acquired data, scout data, and modified data, shown in FIGS. 4B, 4C and 4C as spectrograms, or portions thereof, are given for illustrative purposes, and are in no way limiting. That is, it may be understood that other types of data may be utilized, processed, displayed, or scaled, including waveform data, spectral data, coherogram data, and so forth.

The above-described systems and methods may be further understood by way of example. This example is offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims. For example, specific examples of brain states, medical conditions, levels of anesthesia or sedation and so on, in association with specific drugs and medical procedures are provided, although it will be appreciated that other drugs, doses, states, conditions and procedures, may be considered within the scope of the present invention. Furthermore, examples are given with respect to specific indicators related to brain states, although it may be understood that other indicators and combinations thereof may also be considered within the scope of the present invention. Likewise, specific process parameters and methods are recited that may be altered or varied based on variables such as signal amplitude, phase, frequency, duration and so forth.

EXAMPLE

To illustrate the relationship between anesthesia-induced brain states and age, we recorded 4-lead EEG data using the Sedline brain function monitor during routine care of patients receiving general anesthesia across a broad range of patient ages, from 0 to 90 years of age. Data were recorded using two different drugs, propofol and sevoflurane, two of the most commonly used anesthetic drugs. In one cohort, we analyzed EEG during maintenance of propofol anesthesia in young adult (age 18-38 years, N=20), middle-aged (age 40-59 years, N=23), and elderly patients (age 60-89 years, N=19). In another cohort, we analyzed EEG during maintenance of sevoflurane anesthesia in young adult (age 18-38 years, N=34), middle-aged (age 40-59 years, N=31), and elderly patients (age 60-89 years, N=32). In another cohort, we analyzed EEG during maintenance of sevoflurane anesthesia in children and young adults (age 0 to 36 years, N=63). In yet another cohort, we analyzed EEG during maintenance of propofol anesthesia in children and young adults (age 0 to 28 years, N=111). We used multitaper spectral and coherence methods to analyze the EEG. The following examples describe the results of these analyses, and illustrate their application in the context of the present invention.

Figure 5:
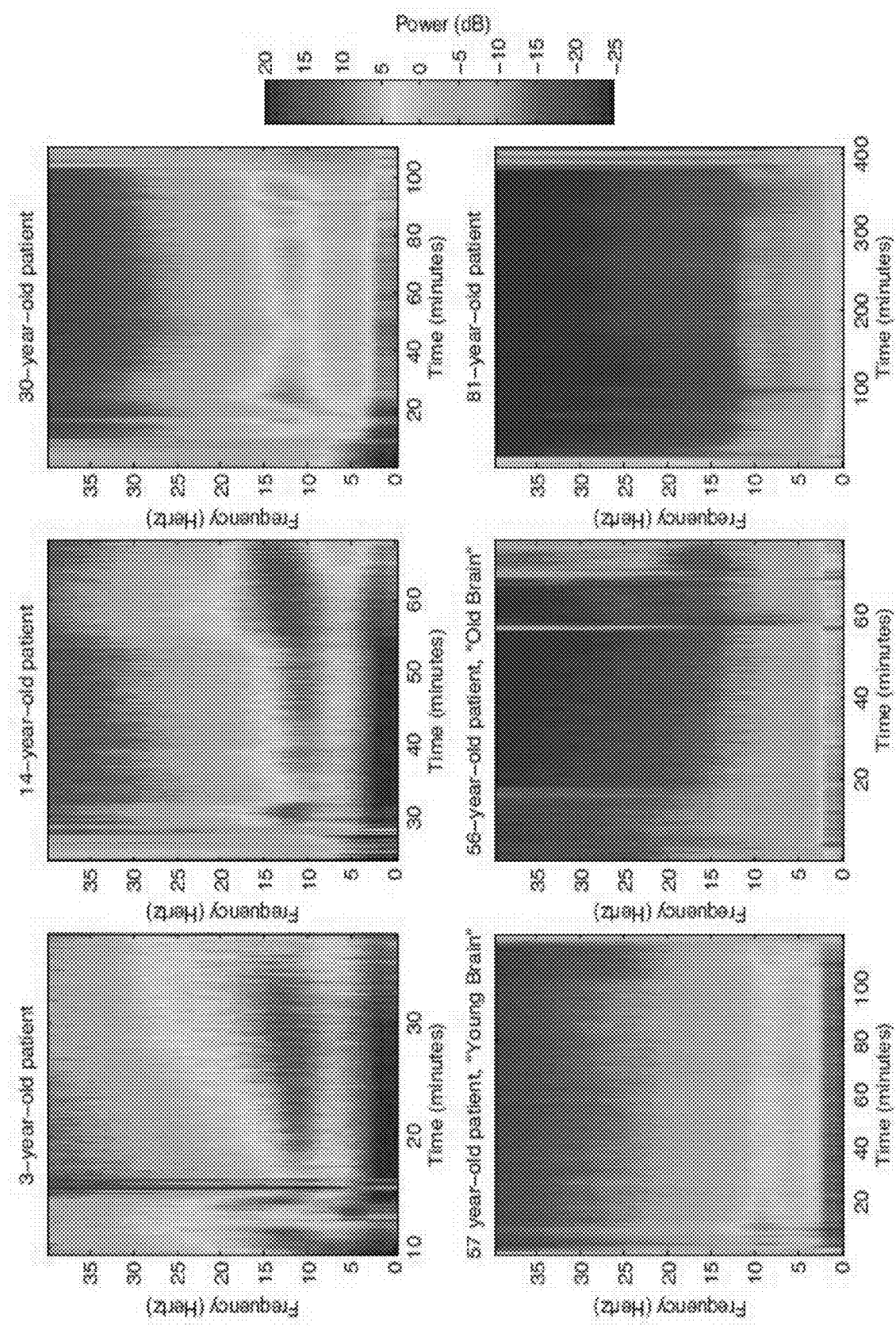
FIG. 5 is an illustration of example EEG spectrograms during propofol-induced general anesthesia across a range of ages, in accordance with the present disclosure.

FIG. 5 shows representative EEG spectrograms during propofol general anesthesia for patients across a wide range of ages from childhood through old age. The spectrogram for the 30 year old patient in this example shows characteristic slow (<1 Hz) and alpha (8-12 Hz) oscillations consistent with the unconscious state during propofol anesthesia. In the 57 year old patient, the same pattern is visible, but in the 81 year old patient, this pattern is faint and difficult to discern because the EEG signal and EEG power are much smaller. With increasing age, patients may experience different rates of aging and cognitive decline. FIG. 5 shows a 56 year old patient whose EEG spectrogram more closely resembles that of the 81-year old patient than the 57 year old patient who is closer in chronological age. This could reflect a higher degree of apparent aging in the 56 year old patient. In children, such as the 3 and 14 year old patients shown in FIG. 6, the EEG power appears to be much larger than in any of the adults across all frequency bands, and appears to decrease with age. Overall, from childhood through old age, the EEG power and EEG signal amplitude decreases by an order of magnitude.

The example shown in FIG. 5, as well as the additional analyses to follow, suggest why existing EEG-based anesthetic monitors that ignore age information are unlikely to accurately represent level of consciousness or anesthesia in children and elderly patients. Specifically, existing EEG-based depth-of-anesthesia monitors compute proprietary indices based on EEG power and functions of EEG power, which are shown herein to be significantly different in children compared to adults, and in elderly adults compared to younger adults. In particular, EEG-based anesthetic monitoring devices often use power in higher-frequency bands, such as beta (12-25 Hz) or gamma (25-40 Hz), to infer when patients are lightly anesthetized, sedated, or recovering consciousness. Since children have much higher EEG power in these bands compared to adults, EEG-based anesthetic devices that do not account for age may incorrectly infer that children are not anesthetized, and compel anesthetists to increase the dose of anesthetic beyond what is actually required, resulting in systematic overdose. EEG-based anesthetic monitoring devices also rely on increased power in lower-frequency EEG bands, such as the slow (0.1 to 1 Hz), delta (1 to 4 Hz), theta (4 to 8 Hz), and alpha (8 to 12 Hz), for instance, to infer that patients are sedated or anesthetized. Since elderly patients tend to have much smaller EEG signals and EEG power compared to younger adults, EEG-based anesthetic devices that do not account for age may sense the reduced EEG power in these frequency bands in elderly patients, and then incorrectly infer that the patients are not anesthetized, compelling anesthetists to increase the dose of anesthetic beyond what is actually required, resulting in systematic overdose. The systems and methods of the present disclosure overcome these limitations by incorporating age information in the assessment of the patient's brain state under anesthesia or sedation. The display scaling example described above and illustrated in FIG. 4C indicates that one way of using age information includes adjusting color scales or scale limits according to age or apparent age, in order to more accurately display EEG and anesthetic brain state information. As described earlier, this information could be used to establish the most appropriate EEG signatures given a patient's age or apparent age, or to estimate the patient's apparent age, or both. Additional examples of how age information could be utilized or estimated are provided below.

Figure 6:
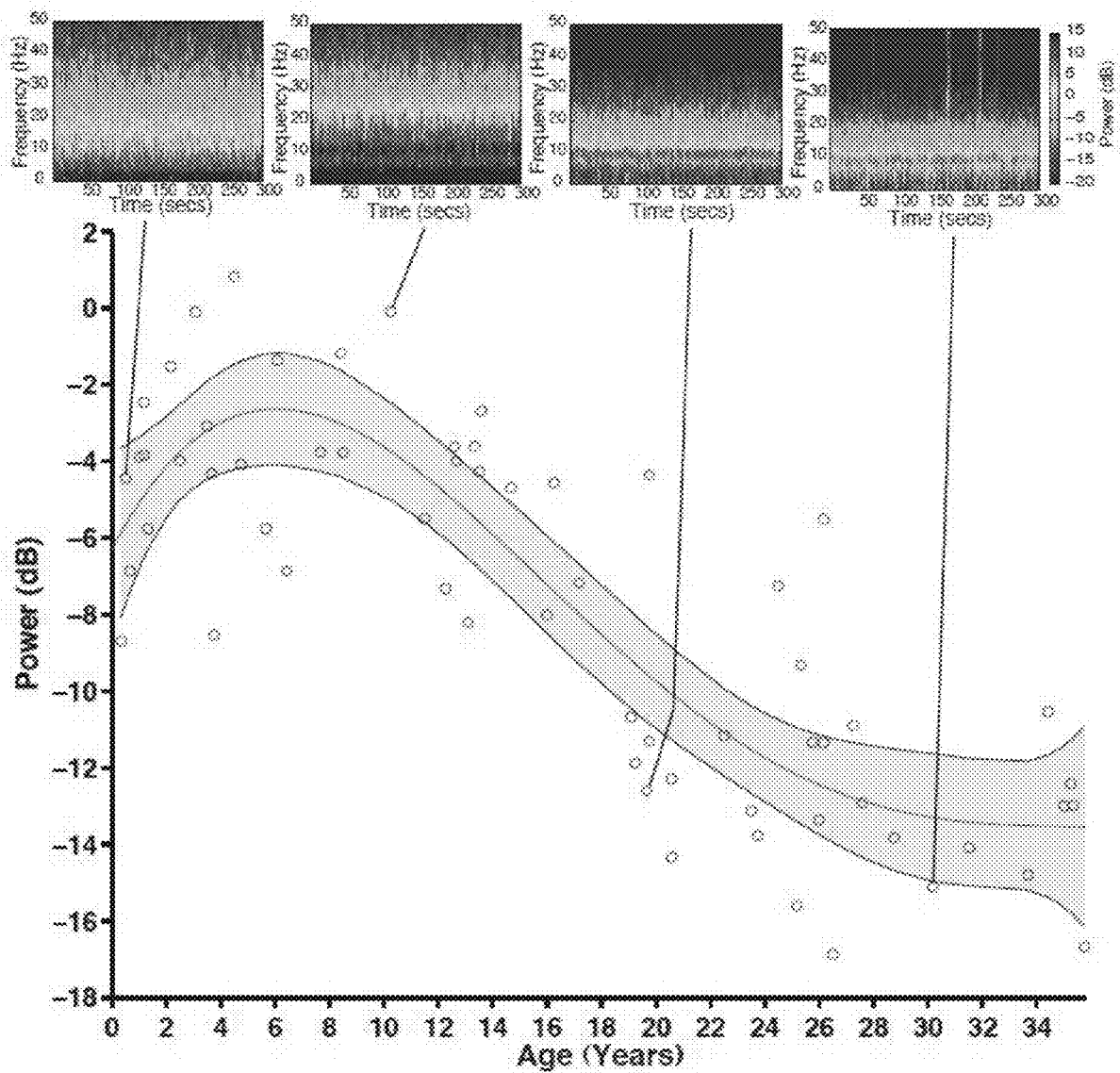
FIG. 6 is a graphical illustration of total EEG power and representative spectrograms in patients of different ages during sevoflurane anesthesia in accordance with the present disclosure.
Figure 7:
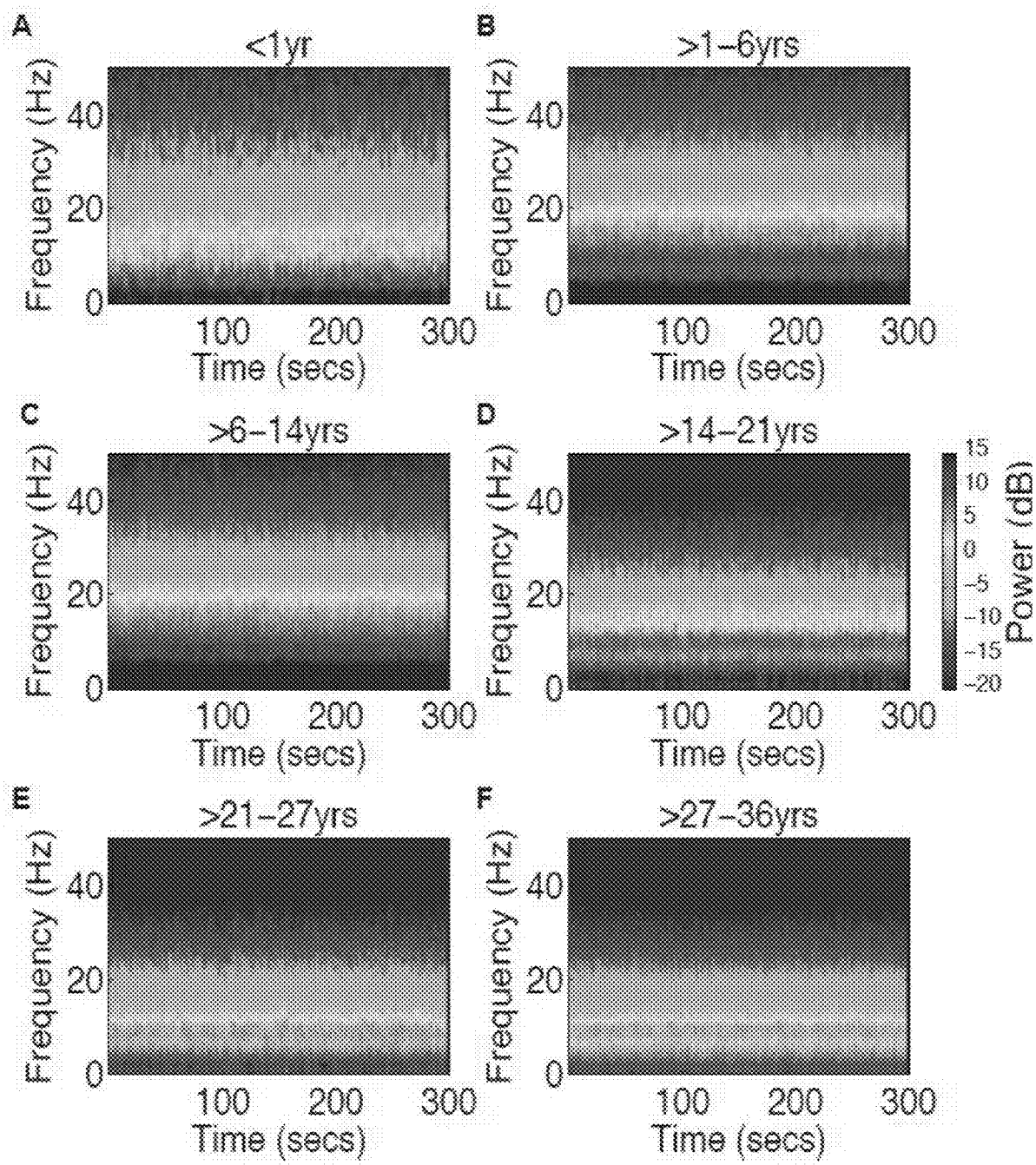
FIG. 7 shows graphical examples illustrating mean EEG spectrograms of patients in different age groups undergoing sevoflurane anesthesia in accordance with the present disclosure.
Figure 8:
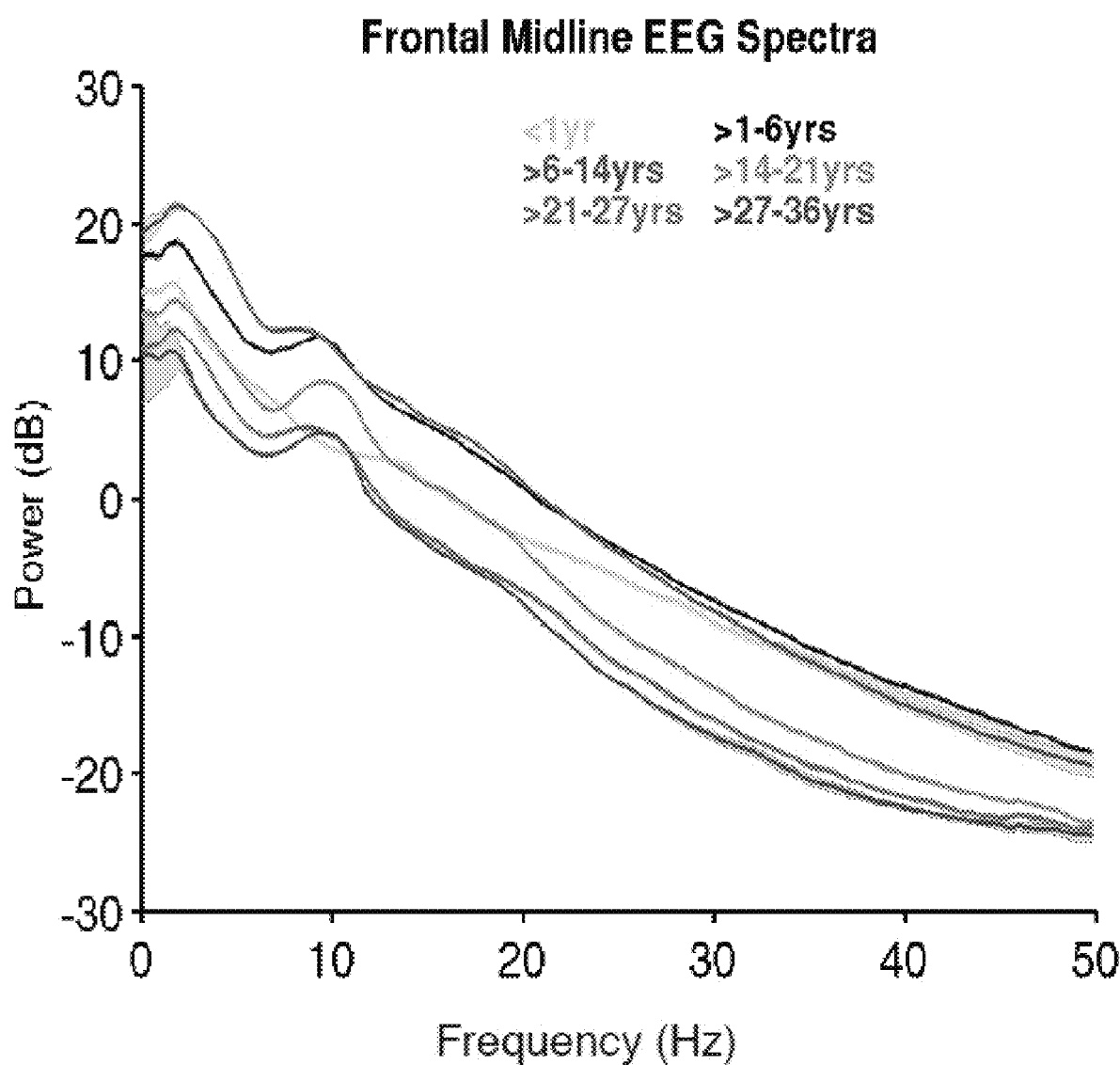
FIG. 8 shows graphical examples illustrating mean EEG spectra of patients in different age groups undergoing sevoflurane anesthesia in accordance with the present disclosure.

FIG. 6 shows the relationship between total EEG power (1-50 Hz) and age, observed in children and young adults during sevoflurane anesthesia (bottom), along with representative spectrograms from individual subjects across this age range (top). FIG. 6 also illustrates that total power increases between the ages of 0 to approximately 6 years of age, and then decreases with increasing age. The form of the EEG spectrum (top row) also changes with age. For children less than 1 year of age (top row, left), the EEG spectrum shows a large concentration of power around approximately 1 Hz that decreases with increasing frequency. The spectrum in older children (top row, $2^{nd}$ panel from the left) shows a form similar to adults (top row, $3^{rd}$, and $4^{th}$ panels from the left), showing peaks in the spectrum at approximately 1 and 10 Hz, but with higher power across all frequencies compared to adults. These age-dependent differences in the form of the spectrogram and spectrum are also illustrated in FIG. 7 and FIG. 8, respectively.

FIG. 6 also illustrates how age information could be used in the present invention. In one mode of operation, the present invention could use the patient's age to select the most appropriate age-dependent EEG signatures. For instance, given the patient's age, the anesthesia-induced EEG signatures associated with that age or age range could be used to infer the patient state. For a patient less than 1 year of age, a different form of EEG spectrum would be associated with the unconscious state (FIG. 6, top row, left), for instance. In another mode of operation, the present invention could analyze the patient's EEG, and use it to infer that patient's apparent age or brain age. For instance, if a patient showed a spectrogram similar in form and power to a child of 10 years (top row, $2^{nd}$ panel from the left), the patient's apparent or developmental age could be characterized as equivalent to a 10 year old. The corresponding anesthesia-induced EEG signatures for a 10 year old could then be used to assess patient brain state during anesthesia. In yet another mode of operation, the present invention could use both the patient's age as well as the patient's EEG to both infer the patient's apparent age or brain age, and to select the most appropriate age-dependent EEG signatures to infer the level of anesthesia or sedation for that patient. For instance, if a patient has a chronological age of approximately 1 year, it is possible that this patient could have a brain response resembling patients less than 1 year, or a brain response that resembles patients between 1 and 2 years of age, depending on that patient's specific level of brain development. Scout data could be analyzed to determine which apparent age, less than 1 year or between 1 and 2 years, most closely matches the given patient. After this determination, the EEG signatures corresponding to the patient's apparent age could be used to assess and monitor the patient's brain state under anesthesia.

Figure 14:
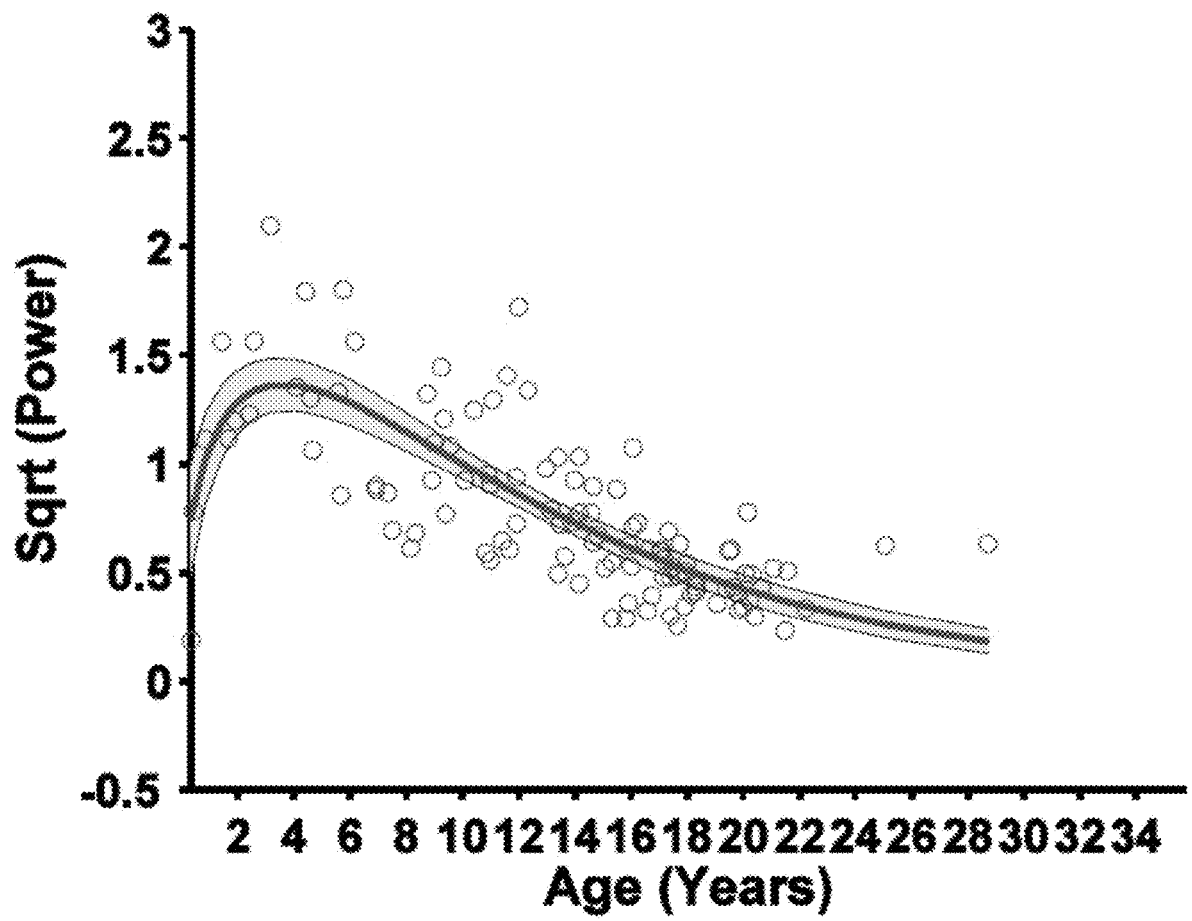
FIG. 14 is a graphical illustration of total EEG power in patients of different ages undergoing propofol anesthesia in accordance with the present disclosure.

As discussed, different modes of operation, in accordance with aspects of the present disclosure, may employ a quantitative or computational representation of the relationship between anesthesia-induced EEG patterns, different brain states or states of consciousness, and age. This quantitative or computational representation could take the form of a database, or a mathematical or statistical model relating EEG patterns and age. FIG. 6 shows how the relationship between total power in the anesthesia-induced unconscious state and age can be represented in terms of a polynomial regression model (lower plot), whose mean (red line) and 95% confidence interval (grey shading) represent the mean power and its distribution, respectively, as a function of age, for instance. Similar representations are illustrated in FIG. 14 (total EEG power versus age in children under propofol), FIG. 15 (EEG slow oscillation power versus age in children under propofol), FIG. 16 (EEG alpha power versus age in children under propofol), and FIG. 17 (EEG total, slow and alpha power versus age in adults under propofol and sevoflurane).

Figure 9:
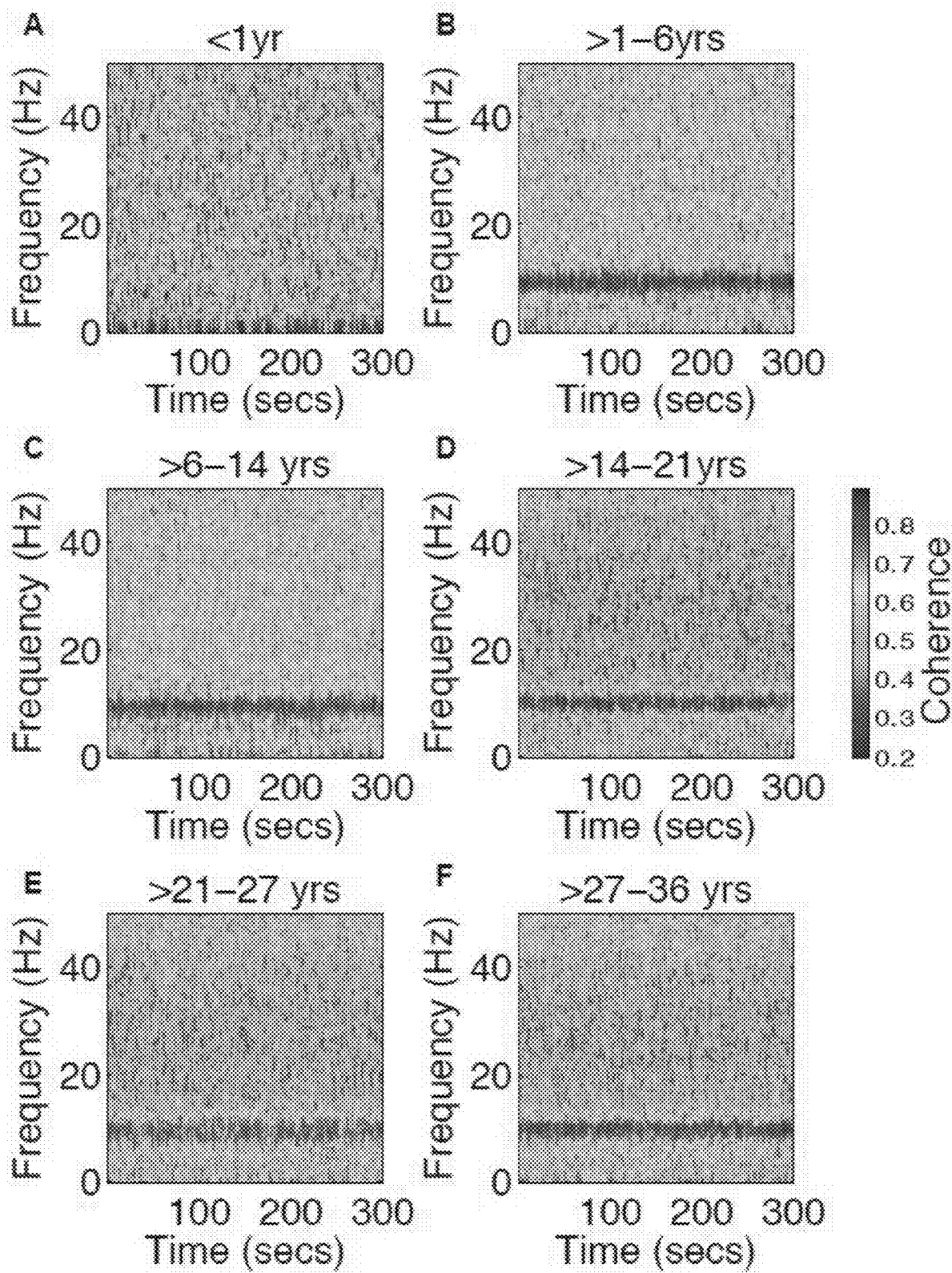
FIG. 9 shows graphical examples illustrating mean EEG coherograms of patients in different age groups undergoing sevoflurane anesthesia in accordance with the present disclosure.
Figure 10:
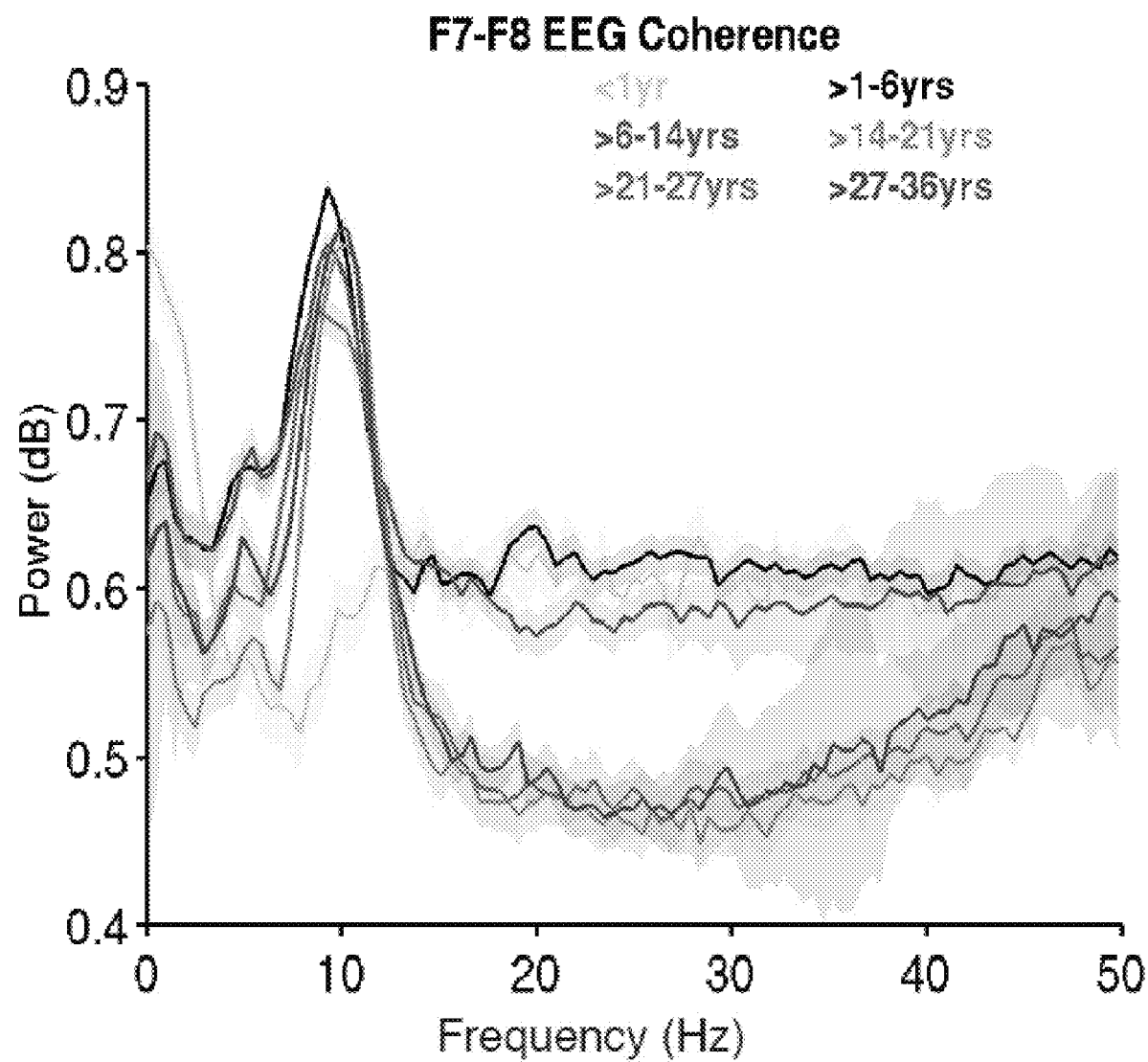
FIG. 10 shows graphical examples illustrating mean EEG coherence of patients in different age groups undergoing sevoflurane anesthesia in accordance with the present disclosure.

Alternatively or concurrently, a comprehensive database of EEG as a function of age could also be used, exemplified in FIG. 6 in terms of the scatter plot (lower plot), where each point represents an EEG record for a given patient at a given age, with total power, and spectrum as well (top row), for instance. Such models could be formulated in terms of continuous functions of age, as shown in FIG. 6 (bottom row), as well as FIG. 14, FIG. 15, FIG. 16, and FIG. 17. Alternatively, this information could be formulated in terms of relevant discrete age ranges, as shown in FIG. 7, which illustrates the mean spectrogram across different age range categories, including <1 year, between 1 and 6 years, 6 and 14 years, and so on, for instance. EEG information is not limited to a spectrogram representation, and could be represented in any number of ways, including a spectral representation (FIG. 8), as well as a cohereogram representation (FIG. 9), or the coherence representation (FIG. 10), for instance.

Figure 11:
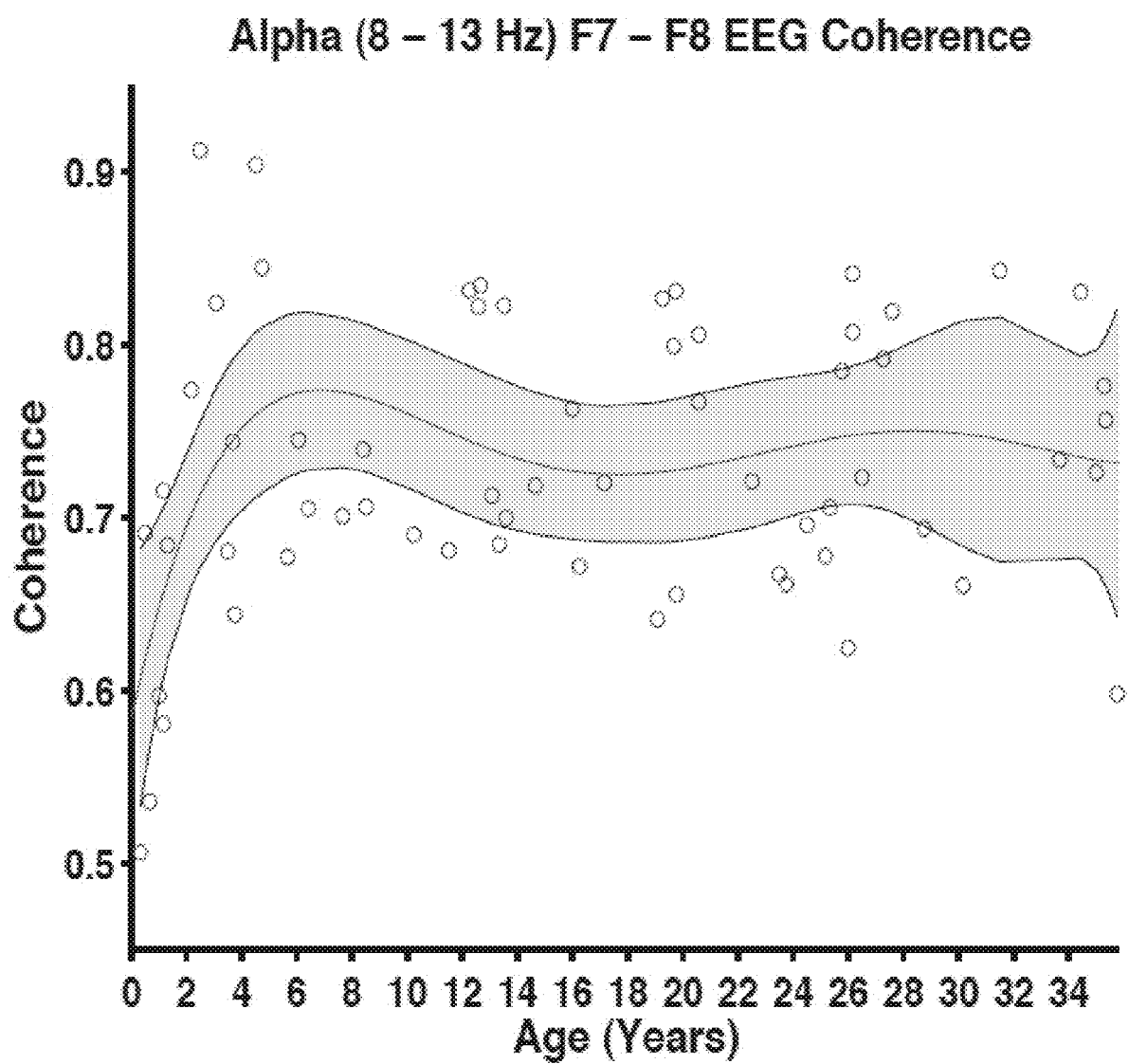
FIG. 11 shows EEG coherence in the alpha frequency band for patients of different ages undergoing sevoflurane anesthesia in accordance with the present disclosure.
Figure 12:
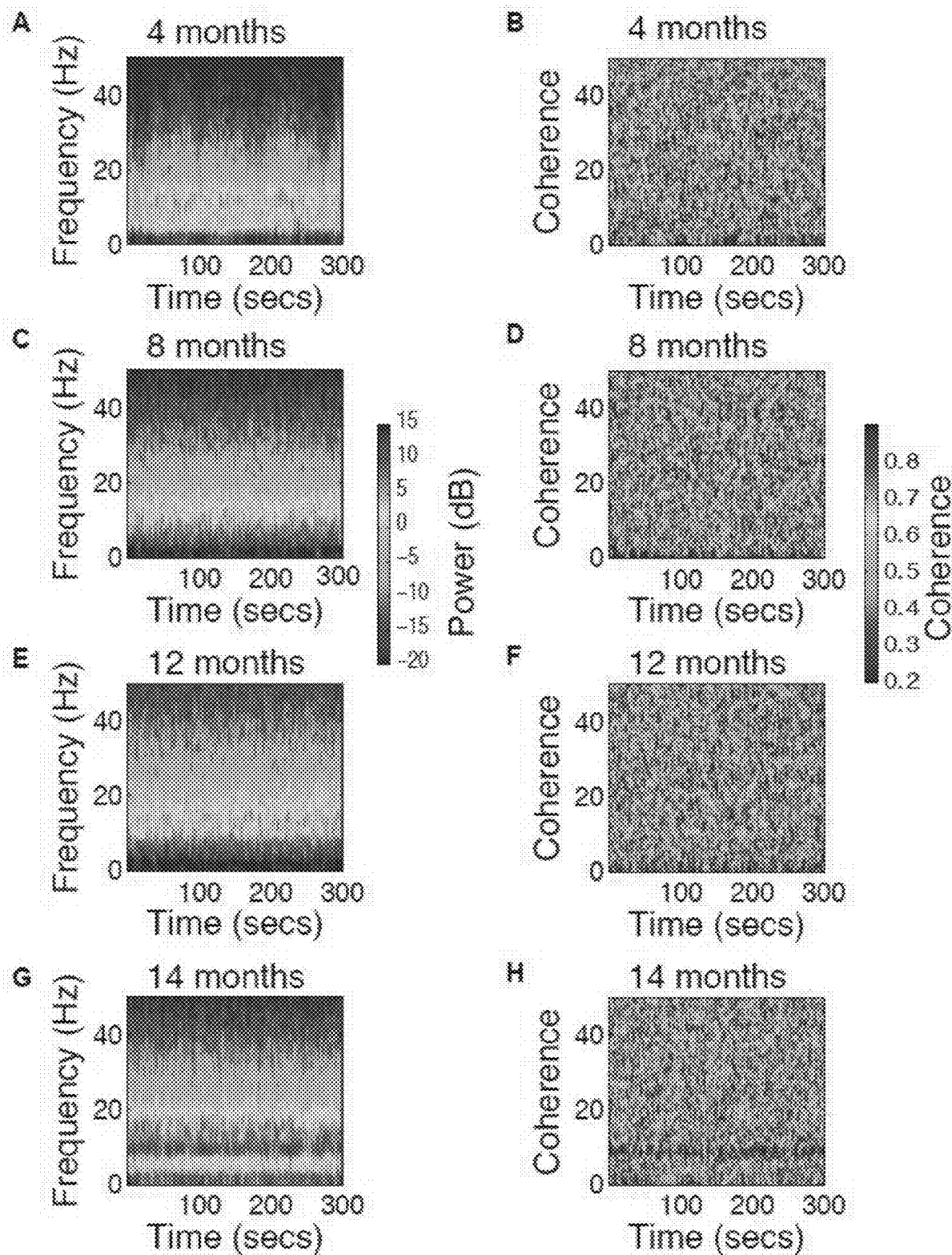
FIG. 12 shows the representative EEG spectrograms and cohereograms in patients 14 months of age or less undergoing sevoflurane anesthesia in accordance with the present disclosure.
Figure 15:
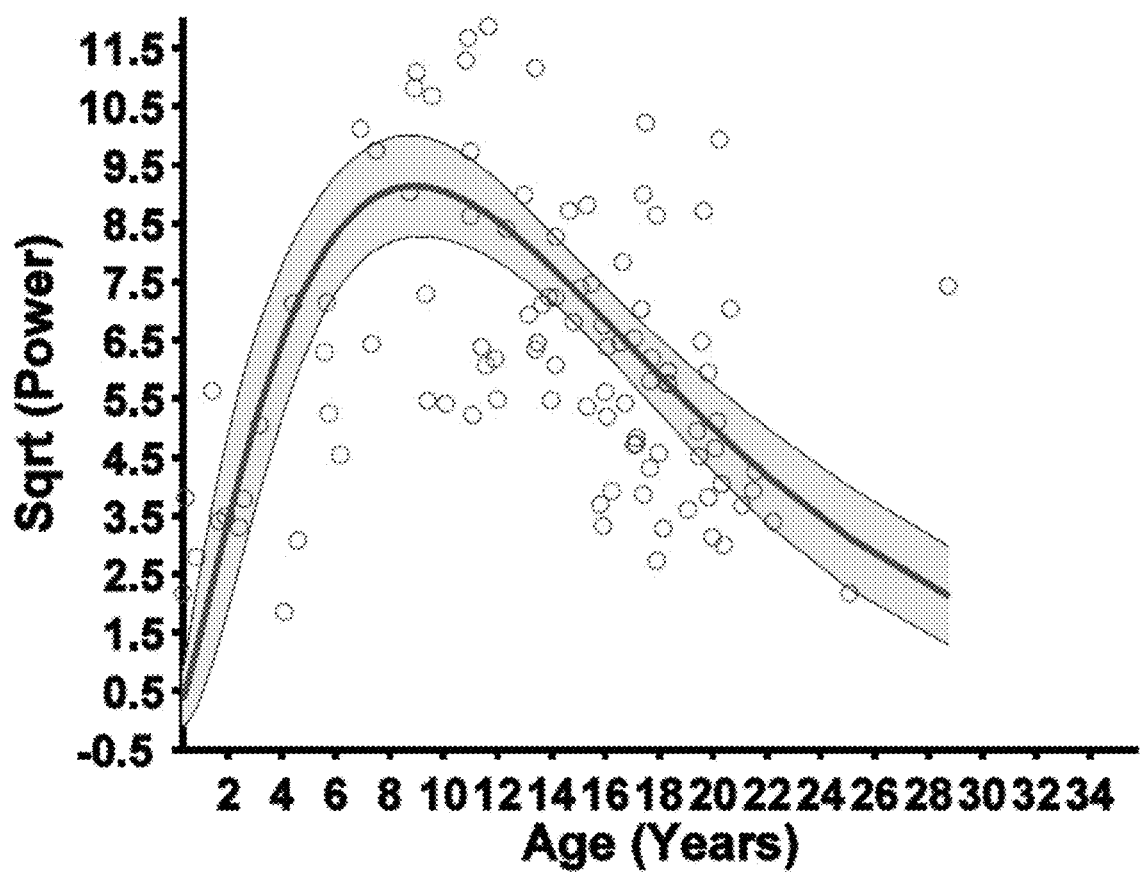
FIG. 15 is a graphical illustration of slow oscillation EEG power in patients of different ages undergoing propofol anesthesia in accordance with the present disclosure.
Figure 16:
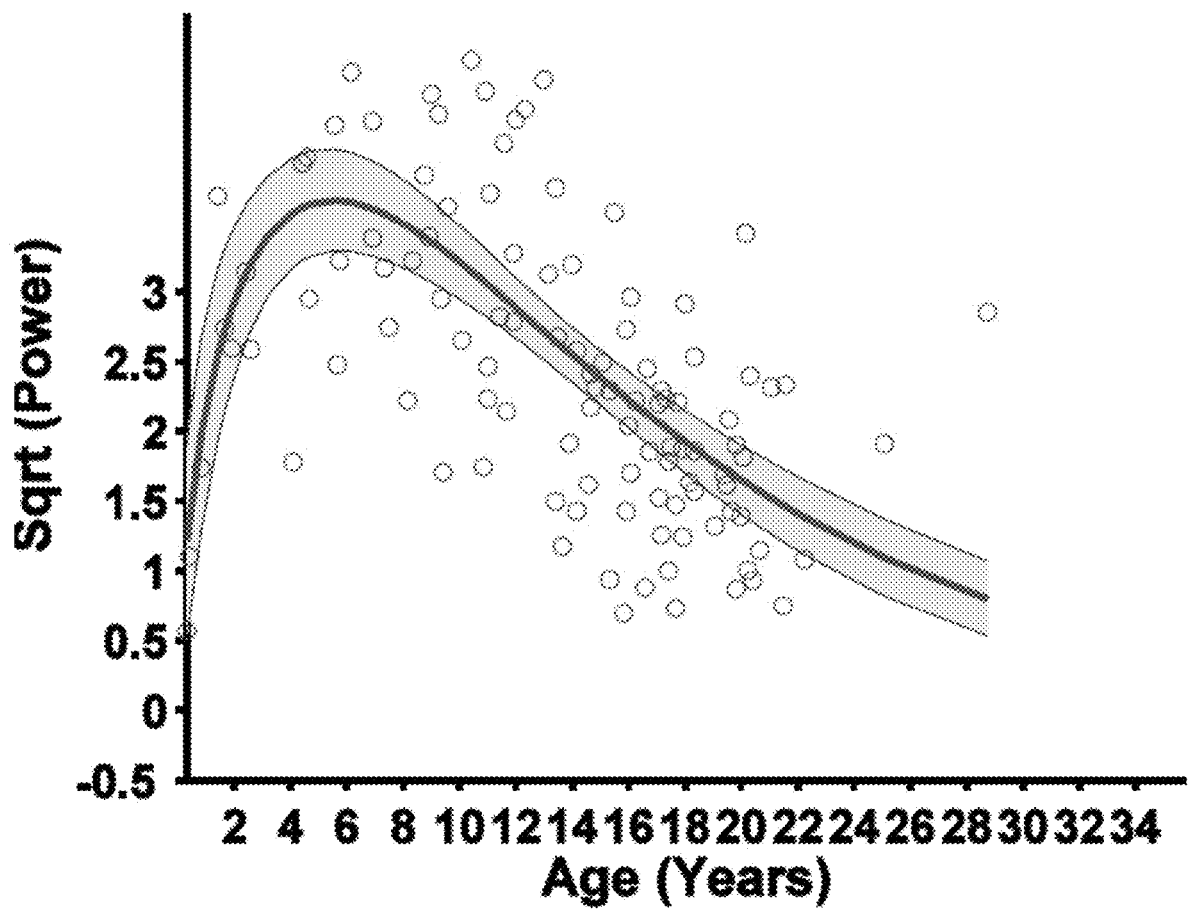
FIG. 16 is a graphical illustration of alpha band EEG power in patients of different ages undergoing propofol anesthesia in accordance with the present disclosure.

Coherence information, as well as any other EEG-based parameter, could also be represented as continuous functions of age, as shown in FIG. 11. The age representation could take on differing levels of detail with respect to age, allowing greater levels of age resolution over age ranges in which brain development is occurring rapidly, for instance. FIG. 12 illustrates how a more detailed month-by-month characterization of both spectrogram (left column) and cohereogram (right column), shown for the anesthetic drug sevoflurane, can be constructed to identify apparent brain age, and characterize the EEG signatures of anesthesia and sedation for a given age or apparent age. FIG. 15 shows an example of how a similar characterization can be used for the drug propofol.

Figure 13:
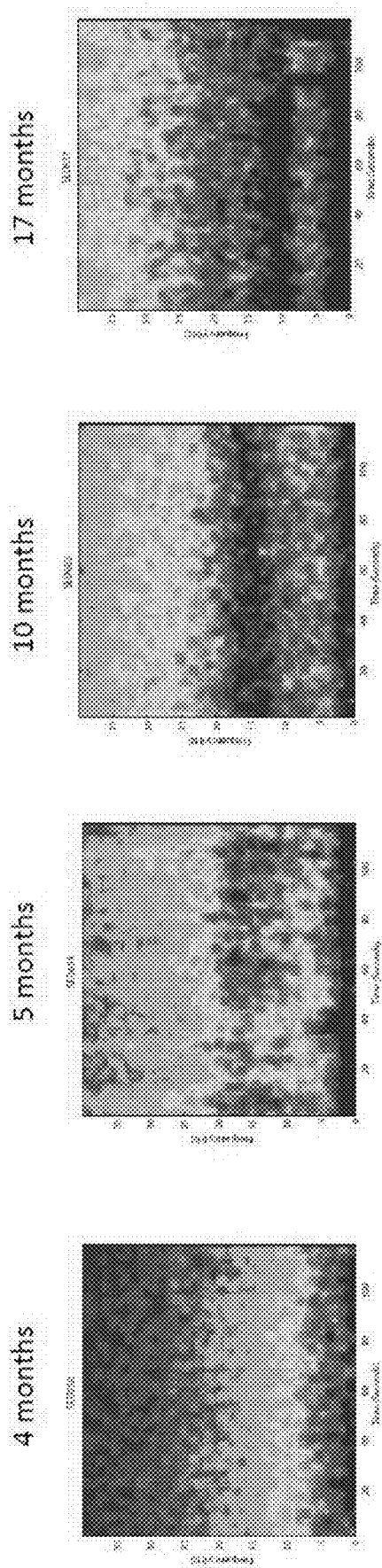
FIG. 13 shows representative EEG spectrograms in patients 17 months of age or less undergoing propofol anesthesia in accordance with the present disclosure.

In addition, in the examples shown in FIGS. 12 and 13, a month-by-month characterization allows for more precise monitoring appropriate to a child patient's unique state of brain development during this period of rapid maturation. As indicated earlier, inferences from using reference information could be made using any number of appropriate established methods, including look-up tables, prediction using a regression or statistical model, perhaps employing Bayesian inference to jointly incorporate age and EEG-related information, machine learning methods, or through cross-correlation, clustering, or related techniques.

Figure 17:
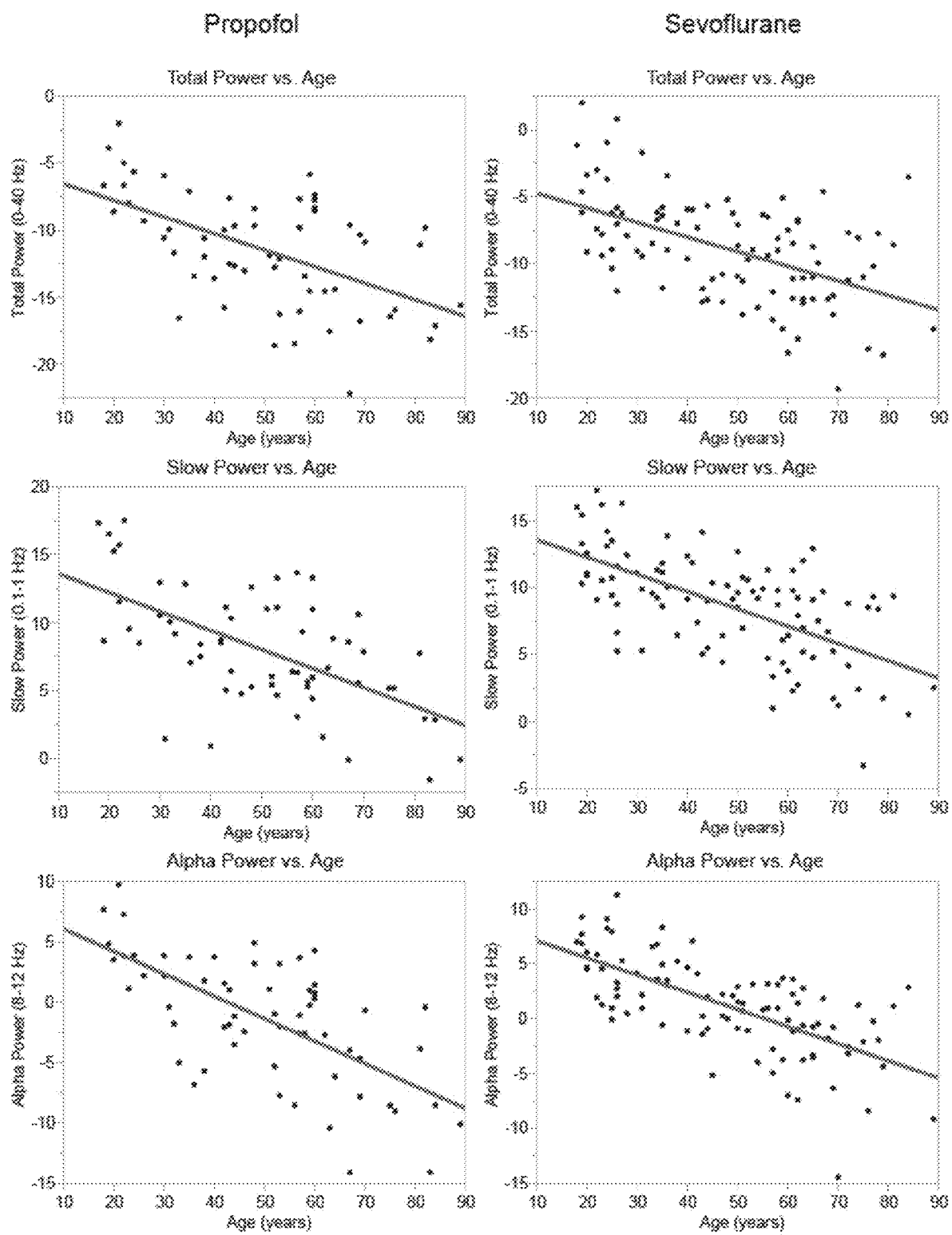
FIG. 17 shows total, slow oscillation, and alpha band EEG power in patients of different ages undergoing propofol and sevoflurane anesthesia in accordance with the present disclosure.

The characterizations specific to the drugs sevoflurane and propofol, shown in FIGS. 12, 13, and 17, express how pertinent covariate information such as drug information can be used. For patients administered sevoflurane, the appropriate sevoflurane database or model could be used, whereas for patients administered propofol the appropriate propofol model or database could be used. Different anesthetic drugs produce different EEG patterns associated with different brain states or states of consciousness, and accounting for these drug-dependent differences in EEG patterns and brain state would be important for accurate assessments of apparent age and age-dependent level of anesthesia. Similarly, the model or database relating EEG features, patient state, and age could include additional patient covariate information such as height, weight or gender, for instance.

These results show that EEG power decreases by orders of magnitude from childhood to adulthood. They also show how very young patients less than one year of age have a different structure in their anesthesia-related EEG oscillations. These age-dependent differences are consistent with know neurobiological changes that occur during development. In very young patients, brain myelination is not significantly developed until approximately 1 year of age. Through progressive development through young adulthood, synapses are pruned by up to 50 percent. Thus, observed age-related changes in anesthesia-induced EEG oscillations may reflect systems-level neuronal changes that occur during development. Similarly, reductions in EEG amplitude during aging in older adults are thought to reflect reductions in grey matter volume, cortical thickness, and reduced synaptic density.

Anesthesia-induced alpha and beta oscillations are thought to occur through resonant cortical and thalamocortical networks potentially involved in top-down modulation of attention and perception. The loss of alpha oscillations in some elderly patients may reflect age-related reductions in cortical and thalamic grey matter and reductions in thalamocortical function. Thus, anatomic and physiological differences between patients of different ages, or those with neurodegenerative or cognitive conditions or disorders, have a profound impact on brain functionality and how anesthetics affect the brain. As a consequence, the assessment of apparent age could be related or represented not just in terms of numerical age, but also in terms of neurological or cognitive conditions related to age, such as developmental stages in children, or age-related conditions such as cognitive impairment, dementia, or Alzheimer's disease, for instance. Referring again to FIG. 5, the 56 year old patient (bottom row, center panel) shows an EEG spectrogram under propofol with dramatically reduced alpha power compared to younger patients, and compared to a 57 year old patient (bottom row, left panel). The reduced propofol-induced alpha power in this 56 year old patient could likely be a consequence of underlying neurobiological changes, such as cortical thinning, grey matter volume reduction, and reduced synaptic density, for instance, that are related to aging, cognitive impairment, and dementia. In such circumstances, the assessment or characterization of apparent age could be characterized in terms of the underlying neurobiological, neurological, or cognitive condition associated with the anesthesia-induced EEG patterns and the patient's chronological age. In this example, we refer to this 56 year old patient as having an "old brain" due to the similarity with the 81 year old patient shown in the same figure (FIG. 5, bottom row, right panel). Refinements in our understanding of the neurobiology of aging, neurodegeneration, and dementia could allow us to refine such characterizations in terms of specific conditions such as mild cognitive impairment, Parkinson's disease, or Alzheimer's disease, for instance. Identification of such conditions, or simply of old apparent age, could help anesthesiologists select specific anesthetic regimens intended to optimize care for these particularly vulnerable patients.

In summary, anatomic and physiological differences between patients of different ages, or those with neurodegenerative or cognitive conditions or disorders, have a profound impact on brain functionality and how anesthetics affect the brain. However there is limited understanding about fundamental brain mechanisms underlying anesthetic drugs. As such, standards of care taking into consideration different requirements in brain monitoring have yet to be established, pointing to the urgent need for an improved understanding of brain physiology under anesthesia and sedation in certain patients. Therefore, promoting a greater understanding of the neuroscience of the aging brain in the anesthesiology community coupled with real-time EEG monitoring, for purposes including titrating anesthetic drug dosing based on observed brain states, are practical first steps to more properly provide anesthesia care for at risk populations.

The present invention recognizes the need for accurate age-appropriate brain monitoring during certain medical procedures, such as general anesthesia and sedation, and therefore provides systems and methods directed to using, determining or inferring age-related information from brain signals. For example, highly structured oscillations in EEG signals that occur during different states of anesthesia-induced sedation and unconsciousness may provide objective neuro-physiological endpoints that could be used to monitor general anesthesia.

In addition, evidence suggests that certain patients, such as the very young and the elderly, may experience adverse neuro-cognitive effects following general anesthesia. Given the anatomic and physiological differences between patients of different ages, it may be appreciated why certain patients are more likely to have postoperative cognitive disorders following anesthesia. This highlights the need for new strategies in relation to anesthesia administration, monitoring and care. The present disclosure therefore provides systems and methods for various applications, including pre-operatively identifying sensitivity to anesthetics and those patients potentially at higher risk for post-operative cognitive conditions or disorders, using such patient-specific information to prescribe specific regimens for anesthetic, post-anesthetic, or intensive care.

Results shown herein illustrate approaches for improving monitoring in elderly patients. For instance, EEG-based anesthetic monitoring devices use the power in lower-frequency EEG bands, such as the slow (0.1 to 1 Hz), delta (1 to 4 Hz), theta (4 to 8 Hz), and alpha (8 to 12 Hz), for instance, to infer that patients are sedated or anesthetized. Because of the much smaller EEG signals and EEG power observed in elderly patients, EEG-based anesthetic devices or systems that do not account for age may sense the reduced EEG power in these frequency bands, and then falsely infer that elderly patients are not anesthetized, compelling anesthetists to increase the dose of anesthetic beyond what is actually required, resulting in systematic overdose. In addition, these results provide important insights into how children could be monitored during GA in the future. Since children and adults have qualitatively similar EEG spectra, it is likely that similar underlying neurophysiological principles apply. A practical approach could entail identifying EEG spectral patterns associated with different anesthetic drugs. Moreover, because anesthesia-induced EEG signals are so much larger in children, the problem of anesthetic brain monitoring may in fact be easier to solve in children than in adults.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for monitoring a patient comprising:
a plurality of sensors configured to at least detect electroencephalogram ("EEG") signals produced by the patient; and
a processor configured to:
generate patient-specific scout data including EEG signals detected by the plurality of sensors from the patient;
determine a power of the patient-specific scout data;
identify an apparent age of the patient using at least the power of the patient-specific scout data; and
control at least one of an acquisition, a processing, or a display scale of EEG data to compensate for an apparent age of the patient.

2. The system of claim 1, wherein the processor is further configured to analyze the power of the patient-specific scout data to identify the apparent age of the patient using at least one of reference listings, look-up tables, or models.

3. The system of claim 2, wherein the processor is further configured to analyze the power in at least one of a slow wave band, a delta band, a theta band, a beta band, and an alpha band.

4. The system of claim 2, wherein the processor is further configured to analyze the power corresponding to a frequency band ranging between 1 and 50 Hz.

5. The system of claim 1, wherein the processor is further configured to determine a brain state of the patient by analyzing the EEG data based on the apparent age of the patient.

6. The system of claim 1, wherein the processor is further configured to determine a state of anesthesia or a state of sedation of the patient by analyzing the EEG data based on the apparent age of the patient.

7. The system of claim 1, wherein the system further comprises a user interface configured to receive patient-specific information.

8. The system of claim 7, wherein the processor is further configured to identify the apparent age using the patient-specific information.

9. The system of claim 1, wherein the system further comprises a display configured to display the EEG data using the display scale controlled in accordance with the apparent age of the patient.

10. The system of claim 1, wherein the processor is further configured to analyze at least one of signal amplitudes, phases, frequencies, power spectra, or drug signatures in patient-specific scout data to further identify the apparent agent of the patient.

11. The system of claim 1, wherein the patient-specific scout data is displayed against a default scale and then displayed against a compensated scale that compensates for the apparent age of the patient.

12. The system of claim 1, wherein patient-specific scout data is displayed against the default scale and EEG signals acquired detected after the patient-specific scout data is displayed against the compensated scale.

13. The system of claim 1, wherein the processor is further configured to use at least one of Bayesian inference, machine learning methods, cross-correlation, or clustering to jointly incorporate age and EEG-related information to identify the apparent age of the patient.

14. The system of claim 1, wherein the processor is further configured to adjust at least one of an amplifier gain or a scale to compensate for an apparent age of the patient.

15. The system of claim 1, wherein the processor is further configured to assemble the EEG signals into time-series data using a multitaper approach to account for a dynamic range of signals spanning several orders of magnitude.

16. The system of claim 1, wherein the processor is further configured to analyze an amplitude of the patient-specific scout data to identify the apparent age of the patient using the patient-specific scout data.

17. The system of claim 1, wherein the processor is further configured to identify age-correlated signal markers from the patient-specific scout data and select a compensated display scale from a plurality of scales based on the age-correlated signal markers.

* * * * *

UNITED STATES PATENT AND TRADEMARK OFFICE
CERTIFICATE OF CORRECTION

PATENT NO. : 10,602,978 B2  
APPLICATION NO. : 14/485523  
DATED : March 31, 2020  
INVENTOR(S) : Patrick L. Purdon et al.

Page 1 of 1

It is certified that error appears in the above-identified patent and that said Letters Patent is hereby corrected as shown below:

In the Specification

Column 7, Line 14, "(3 years)" should be --($\geq$73 years)--.

Signed and Sealed this  
Twenty-sixth Day of May, 2020

Andrei Iancu  
*Director of the United States Patent and Trademark Office*